United States Patent
Abbondanza et al.

(10) Patent No.: US 10,312,395 B2
(45) Date of Patent: Jun. 4, 2019

(54) LUMINESCENT SOLAR CONCENTRATOR COMPRISING DISUBSTITUTED BENZOHETERODIAZOLE COMPOUNDS

(71) Applicant: ENI S.p.A., Rome (IT)

(72) Inventors: Luigi Abbondanza, Novara (IT); Antonio Alfonso Proto, Novara (IT); Giuliana Schimperna, Novara (IT); Liliana Gila, Casalino (IT)

(73) Assignee: Eni S.p.A., Rome (IT)

(*) Notice: Subject to any disclaimer, the term of this patent is extended or adjusted under 35 U.S.C. 154(b) by 0 days.

(21) Appl. No.: 15/514,393

(22) PCT Filed: Sep. 24, 2015

(86) PCT No.: PCT/EP2015/071961
§ 371 (c)(1),
(2) Date: Mar. 24, 2017

(87) PCT Pub. No.: WO2016/046310
PCT Pub. Date: Mar. 31, 2016

(65) Prior Publication Data
US 2017/0250300 A1    Aug. 31, 2017

(30) Foreign Application Priority Data

Sep. 25, 2014  (IT) .............................. MI2014A1662
May 27, 2015  (IT) ........................ 102015000018310

(51) Int. Cl.
*H01L 31/055*     (2014.01)
*C07D 417/14*     (2006.01)
(Continued)

(52) U.S. Cl.
CPC .......... *H01L 31/055* (2013.01); *C07D 413/14* (2013.01); *C07D 417/14* (2013.01);
(Continued)

(58) Field of Classification Search
None
See application file for complete search history.

(56) References Cited

U.S. PATENT DOCUMENTS

| | | | | |
|---|---|---|---|---|
| 2003/0193043 A1* | 10/2003 | Chang | .................. | C07D 471/04 252/582 |
| 2012/0086028 A1* | 4/2012 | Beeson | ................. | H01L 33/501 257/98 |

FOREIGN PATENT DOCUMENTS

| WO | 2011/048458 | 4/2011 |
|---|---|---|
| WO | 2012/007834 A1 | 1/2012 |

(Continued)

OTHER PUBLICATIONS

International Search Report and Written Opinion dated Jan. 4, 2016 for PCT/EP2015/071961.
(Continued)

*Primary Examiner* — Jayne L Mershon
(74) *Attorney, Agent, or Firm* — Abel Schillinger, LLP

(57) ABSTRACT

Luminescent solar concentrator (LSC) comprising at least one disubstituted benzoheterodiazole compound of general formula (I), in which: —Z represents a sulfur atom, an oxygen atom, a selenium atom; or an $NR_6$ group in which $R_6$ is selected from linear or branched $C_1$-$C_{20}$, preferably $C_1$-$C_8$, alkyl groups, or from optionally substituted aryl groups; —$R_1$, $R_2$ and $R_3$, which are the same or different, represent a hydrogen atom; or are selected from linear or branched $C_1$-$C_{20}$, preferably $C_1$-$C_8$, alkyl groups, optionally containing heteroatoms, optionally substituted cycloalkyl groups, optionally substituted aryl groups, optionally substituted linear or branched $C_1$-$C_{20}$, preferably $C_1$-$C_8$, alkoxyl groups, optionally substituted phenoxyl groups, or —$COOR_7$ groups or —$OCOR_7$ groups in which $R_7$ is selected from linear or branched $C_1$-$C_{20}$, preferably $C_1$-$C_8$, alkyl groups, or is a cyano group, provided that when the substituents $R_1$ represents a hydrogen atom, at least one of the substituents $R_2$ and $R_3$ represents an optionally substituted aryl group or an optionally substituted phenoxyl group;

(Continued)

Figure 1:
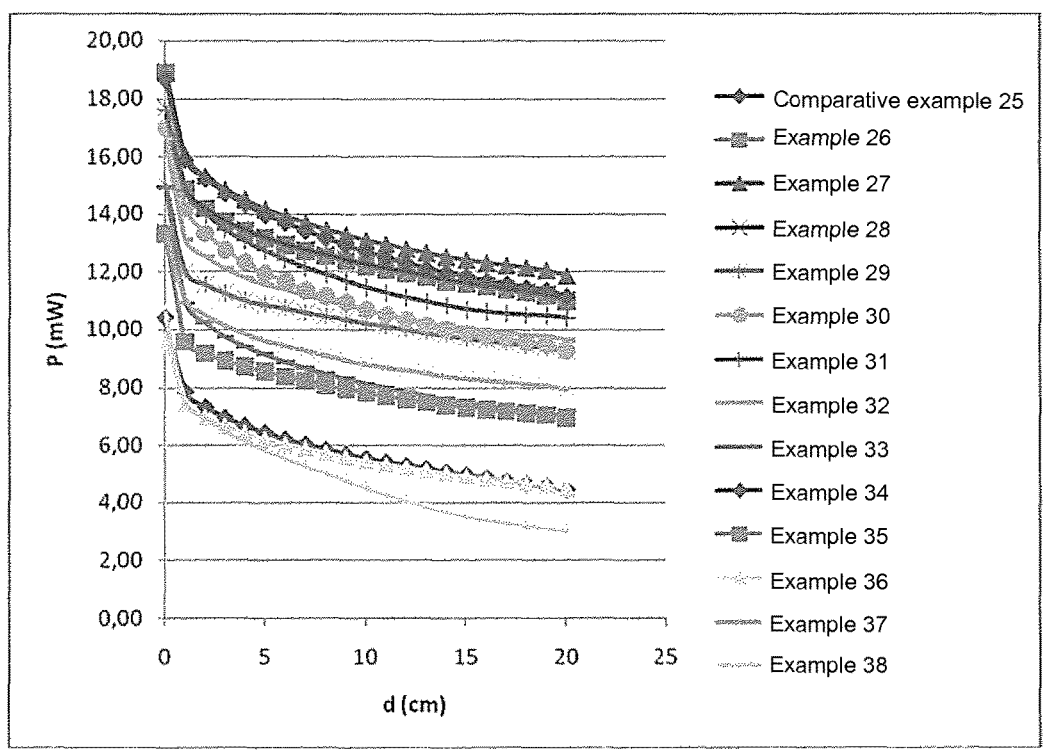

—or $R_1$ and $R_2$, can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium; —or $R_2$ and $R_3$ can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium; —$R_4$ and $R_5$, which are the same or different, represent a hydrogen atom; or are selected from linear or branched $C_1$-$C_{20}$, preferably $C_1$-$C_8$, alkyl groups, optionally containing heteroatoms, optionally substituted cycloalkyl groups, optionally substituted aryl groups, optionally substituted linear or branched $C_1$-$C_{20}$, preferably $C_1$-$C_8$, alkoxyl groups, —$COOR_7$ groups or —$OCOR_7$ groups in which $R_7$ is selected from linear or branched $C_1$-$C_{20}$, preferably $C_1$-$C_8$, alkyl groups, or is a cyano group; or $R_4$ and $R_5$, can optionally be linked together so as to form, together with the carbon atoms to which they are linked, a saturated, unsaturated, or aromatic cyclic ring or a polycyclic system containing from 3 to 14 carbon atoms, preferably from 4 to 6 carbon atoms, containing one or more heteroatoms such as, for example, sulfur, nitrogen, silicon, phosphorus, selenium.

7 Claims, 2 Drawing Sheets

(51) Int. Cl.
*C07D 413/14* (2006.01)
*C09K 11/06* (2006.01)

(52) U.S. Cl.
CPC ...... *C09K 11/06* (2013.01); *C09K 2211/1007* (2013.01); *C09K 2211/1014* (2013.01); *C09K 2211/1048* (2013.01); *C09K 2211/1051* (2013.01); *C09K 2211/1092* (2013.01); *Y02E 10/52* (2013.01)

(56) References Cited

FOREIGN PATENT DOCUMENTS

WO 2013/005177 A2 1/2013
WO 2013/02135 2/2013

OTHER PUBLICATIONS

Blouin N. et al. in "Journal of the American Chemical Society" (2008), vol. 130, p. 732-742.
Zeng S. et al. in "Dyes and Pigments" (2012), vol. 95, Issue 2, p. 229-235.
Zhang M. et al. in "Journal of the American Chemical Society" (2007), vol. 129(12), p. 3472-3473.
Ohshimizu K. et al. in "Macromolecules" (2011), vol. 44(4), p. 719-727.
Lee W. et al. in "Tetrahedron" (2013), vol. 69, p. 9175-9182.
Blouin N. et al. in "Journal of American Chemical Society" (2008), vol. 130, p. 732-742.

* cited by examiner

LUMINESCENT SOLAR CONCENTRATOR COMPRISING DISUBSTITUTED BENZOHETERODIAZOLE COMPOUNDS

The present invention relates to luminescent solar concentrators (LSC) comprising at least one disubstituted benzoheterodiazole compound.

The present invention also relates to the use of at least one disubstiututed benzoheterodiazole compound in the construction of luminescent solar concentrators (LSCs).

The said luminescent solar concentrators (LSC) can advantageously be used in the construction of photovoltaic devices (or solar devices).

As a consequence, the present invention also relates to a photovoltaic device (or solar device) comprising at least one photovoltaic cell (or solar cell) and at least one luminescent solar concentrator (LSC) including at least one disubstituted benzoheterodiazole compound.

In the state of the art, one of the main limitations on utilization of the energy of solar radiations is the ability of photovoltaic devices (or solar devices) to absorb optimally only radiations having wavelengths falling within a narrow spectral range.

In comparison with the spectral range of solar radiation which extends from wavelengths of approximately 300 nm to wavelengths of approximately 2500 nm, photovoltaic cells (or solar cells) based on crystalline silicon, for example, have an optimum absorption zone (effective spectrum) in the range 900 nm-1100 nm, while polymer photovoltaic cells (or solar cells) are likely to become damaged if exposed to radiations having a wavelength less than approximately 500 nm because of the photodegradation phenomena caused, which become significant below that limit. Typically, the efficiency of photovoltaic devices (or solar devices) according to the state of the art is a maximum in the spectral region ranging from 570 nm to 680 nm (yellow-orange).

The abovementioned disadvantages bring about limited external quantum efficiency (EQE) in photovoltaic devices (or solar devices), defined as the ratio between the number of electron-hole pairs generated in the semiconductor material of photovoltaic devices (or solar devices) and the number of photons incident on the said photovoltaic devices (or solar devices).

A number of devices placed between the light radiation source (the sun) and the photovoltaic devices (or solar devices) have been developed to improve the external quantum efficiency (EQE) of photovoltaic devices (or solar devices); these selectively absorb incident radiation having wavelengths outside the effective spectrum of the said photovoltaic devices (or solar devices), emitting the absorbed energy in the form of photons having a wavelength falling within the effective spectrum. Said devices are known as luminescent solar concentrators (LSCs). When the energy of the photons re-emitted from the luminescent solar concentrators (LSCs) is higher than that of the incident photons, the process of photoluminescence, comprising absorption of the solar radiation and subsequent re-emission of photons having a shorter wavelength, is also known as the "up-conversion" process. Conversely, when the energy of the photons emitted by the luminescent solar concentrators (LSCs) is lower than that of the incident photons, the photoluminescent process is defined as a "down-conversion" (or "down-shifting") process. Generally, the said luminescent solar concentrators (LSCs) comprise large sheets of a material which is transparent to solar radiation (for example, polymer or inorganic glasses) within which fluorescent compounds acting as spectrum converters are dispersed or chemically bonded to said material. As a result of the effect of the optical phenomenon of total reflection the radiation emitted by the fluorescent compounds is "guided" towards the thin edges of the sheet where it is concentrated on photovoltaic cells (or solar cells) located there. In this way, extensive surface areas of low cost material (the photoluminescent sheets) can be used to concentrate light onto the small surface areas of high cost materials [photovoltaic cells (or solar cells)].

The fluorescent compounds can be deposited on the glass substrate in the form of thin film or, as in the case of polymer materials, they can be dispersed within the polymer matrix. Alternatively, the polymer matrix can be directly functionalized with fluorescent chromophor groups.

Ideally, for use in spectrum converters, fluorescent compounds must have the following properties:

a high luminescence quantum efficiency ($\Phi$) [($\Phi$) is defined according to equation (1) shown below as the ratio between the number of photons emitted and the number of photons adsorbed by a luminescent molecule per unit time, and has a maximum value of 1:

($\Phi$)=number of photons emitted/number of photons absorbed   (1);

a wide absorption band in the spectral region within which the photovoltaic device (or solar device) is not very efficient;
a high absorption coefficient;
a narrow emission band in the spectral region in which the photovoltaic device (or solar device) is mostly efficient;
well-separated absorption and emission bands to prevent or minimize autoabsorption phenomena.

It is known that some benzothiadiazole compounds, in particular 4,7-di-(thien-2'-yl)-2,1,3-benzothiadiazole (DTB), are fluorescent compounds which can be used in the construction of luminescent solar concentrators (LSCs). Compounds of this type have been described in International Patent Application WO 2011/048458 in the name of the Applicant.

4,7-di-(thien-2'-yl)-2,1,3-benzothiadiazole (DTB) is characterized by emission centred around 579 nm, a value corresponding to an energy well above the minimum functioning threshold of photovoltaic cells (or solar cells), a threshold which, for example, corresponds to a wavelength of around 1100 nm in the case of the most widely used photovoltaic cells (or solar cells) based on silicon. In addition, its light radiation absorption is intense and extensive over a relatively wide range of wavelengths, ranging indicatively from 550 nm (the wavelength of green radiation) to the ultraviolet. Finally, 4,7-di-(thien-2'-yl)-2,1,3-benzothiadiazole (DTB) has a Stokes shift in dichloromethane solution of 134 nm, which is very much higher than that of most commercial products hitherto proposed for use in luminescent solar concentrators (LSCs).

For these reasons, the use of 4,7-di-(thien-2'-yl)-2,1,3-benzothiadiazole (DTB) has made it possible to construct luminescent solar concentrators (LSCs) of excellent quality.

Although absorbing a significant part of the solar spectrum, 4,7-di-(thien-2'-yl)-2,1,3-benzothiadiazole (DTB) nevertheless has modest absorption in regions of greater wavelength, corresponding to yellow and red radiations, which cannot therefore be converted into others which can be more effectively utilized by a photovoltaic cell (or solar cell).

The Applicant has therefore set itself the problem of finding fluorescent compounds which are capable of providing performances which are comparable to or even better than those of known benzothiadiazole compounds, in particular in terms of the power generated by the photovoltaic devices in which they are used.

The Applicant has now found that disubstituted benzoheterodiazole compounds having a specific general formula (i.e. of general formula (I) indicated below) can be advantageously used in the construction of luminescent solar concentrators (LSCs). The said luminescent solar concentrators (LSCs) can in turn be advantageously used, for example, together with photovoltaic cells (or solar cells) in the construction of photovoltaic devices (or solar devices). The said disubstituted benzoheterodiazole compounds are capable of providing performances which are comparable to or even better than those of known benzothiadiazole compounds, in particular in terms of the power generated by the photovoltaic devices in which they are used. Moreover, the Applicant has found that the said disubstituted benzoheterodiazole compounds have excellent photostability and, therefore, higher durability over time.

The object of the present invention therefore relates to a luminescent solar concentrator (LSC) comprising at least one disubstituted benzoheterodiazole compound of general formula (I):

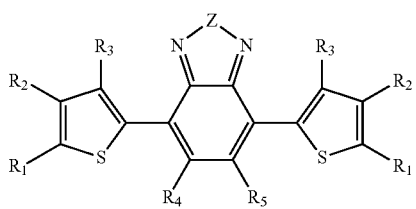

(I)

in which:
- Z represents a sulfur atom, an oxygen atom, a selenium atom; or an $NR_6$ group in which $R_6$ is selected from linear or branched $C_1$-$C_{20}$, preferably $C_1$-$C_8$, alkyl groups, or from optionally substituted aryl groups;
- $R_1$, $R_2$ and $R_3$, which are the same or different, represent a hydrogen atom; or are selected from linear or branched $C_1$-$C_{20}$, preferably $C_1$-$C_8$, alkyl groups, optionally containing heteroatoms, optionally substituted cycloalkyl groups, optionally substituted aryl groups, optionally substituted linear or branched $C_1$-$C_{20}$, preferably $C_1$-$C_8$, alkoxyl groups, optionally substituted phenoxyl groups, or —$COOR_7$ groups or —$OCOR_7$ groups in which $R_7$ is selected from linear or branched $C_1$-$C_{20}$, preferably $C_1$-$C_8$, alkyl groups, or is a cyano group, provided that when the substituents $R_1$ represents a hydrogen atom, at least one of the substituents $R_2$ and $R_3$ represents an optionally substituted aryl group or an optionally substituted phenoxyl group;
- or $R_1$ and $R_2$, can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- or $R_2$ and $R_3$ can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- $R_4$ and $R_5$, which are the same or different, represent a hydrogen atom; or are selected from linear or branched $C_1$-$C_{20}$, preferably $C_1$-$C_8$, alkyl groups, optionally containing heteroatoms, optionally substituted cycloalkyl groups, optionally substituted aryl groups, optionally substituted linear or branched $C_1$-$C_{20}$, preferably $C_1$-$C_8$, alkoxyl groups, —$COOR_7$ groups or —$OCOR_7$ groups in which $R_7$ is selected from linear or branched $C_1$-$C_{20}$, preferably $C_1$-$C_8$, alkyl groups, or is a cyano group;
- or $R_4$ and $R_5$, can optionally be linked together so as to form, together with the carbon atoms to which they are linked, a saturated, unsaturated, or aromatic cyclic ring or a polycyclic system containing from 3 to 14 carbon atoms, preferably from 4 to 6 carbon atoms, containing one or more heteroatoms such as, for example, sulfur, nitrogen, silicon, phosphorus, selenium.

In accordance with a preferred embodiment of the present invention, in said general formula (I):
- Z represents a sulfur atom or an oxygen atom;
- $R_1$, which are the same, represent a hydrogen atom; or are selected from optionally substituted aryl groups, preferably are phenyl, 2,5-dimethylphenyl, 2,6-dimethylphenyl, 2,6-di-iso-propylphenyl, 2,5-dimethoxyphenyl, 2,6-dimethoxyphenyl, 2,4-dimethoxyphenyl;
- $R_2$ and $R_3$, which are the same or different, represent a hydrogen atom; or are selected from linear or branched $C_1$-$C_{20}$, preferably $C_1$-$C_8$, alkyl groups, preferably are methyl; or are selected from optionally substituted aryl groups, preferably are phenyl, 2,6-dimethylphenyl, 2-phenoxyphenyl; or are selected from optionally substituted phenoxyl groups, preferably are phenoxyl;
- $R_4$ and $R_5$, which are the same, represent a hydrogen atom.

For the purpose of the present description and of the following claims the definitions of numerical intervals always comprise the end numbers unless specified otherwise.

For the purpose of the present description and of the following claims the term "comprising" also includes the terms "which essentially consists of" or "which consists of".

The term "$C_1$-$C_{20}$ alkyl groups" means alkyl groups having from 1 to 20 carbon atoms, linear or branched. Specific examples of $C_1$-$C_{20}$ alkyl groups are: methyl, ethyl, n-propyl, iso-propyl, n-butyl, iso-butyl, t-butyl, pentyl, 2-ethyl-hexyl, hexyl, heptyl, octyl, nonyl, decyl, dodecyl.

The term "$C_1$-$C_{20}$ alkyl groups optionally containing heteroatoms" means alkyl groups having from 1 to 20 carbon atoms, linear or branched, saturated or unsaturated, in which at least one of the hydrogen atoms is replaced with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichlororoethyl, 2,2,3,3-tetrafluoropropyl, 2,2,3,3,3-pentafluoropropyl, perfluoropentyl, perfluorooctyl, perfluorodecyl, oxymethyl, thiomethyl, thioethyl, dimethylamino, propylamino, dioctylamino.

The term "cycloalkyl groups" means cycloalkyl groups having from 3 to 10 carbon atoms. Said cycloalkyl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups; aryl groups. Specific examples of cycloalkyl groups are: cyclopropyl, 1,4-dioxin, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl groups" means aromatic carbocyclic groups. Said aryl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups; aryl groups. Specific examples of aryl groups are: phenyl, 2,5-dimethylphenyl, 2,6-dimethylphenyl, 2,6-di-isopropylphenyl, 2,5-dimethoxyphenyl, 2,6-dimethoxyphenyl, 2,4-dimethoxyphenyl, trimethylphenyl, methoxyphenyl, hydroxyphenyl, 2-phenoxyphenyl, fluorophenyl, pentafluorophenyl, chlorophenyl, nitrophenyl, dimethylaminophenyl, naphthyl, phenylnaphthyl, phenanthrene, anthracene.

The term "$C_1$-$C_{20}$ alkoxyl groups" means alkoxyl groups having from 1 to 20 carbon atoms, linear or branched. Said alkoxyl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups. Specific examples of $C_1$-$C_{20}$ alkoxyl groups are: methoxyl, ethoxyl, fluoroethoxyl, n-propoxyl, iso-propoxyl, n-butoxyl, n-fluoro-butoxyl, iso-butoxyl, t-butoxyl, pentoxyl, hexoxyl, heptyloxyl, octyloxyl, nonyloxyl, decyloxyl, dodecyloxyl.

The term "phenoxyl groups which can be substituted" means phenoxyl groups $C_6H_5O$ which can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; aryl groups; cyano groups; amine groups; nitro groups. Specific examples of phenoxyl groups $C_6H_5O$ are: phenoxyl, 4-nitro-phenoxyl, 2,4-d i-nitrophenoxyl, 2-chloro-4-nitrophenoxyl, 2-fluoro-4-nitrophenoxyl, 3-fluoro-4-nitrophenoxyl, 2-hydroxymethyl-4-nitrophenoxyl, 3-hydroxymethyl-4-nitrophenoxyl, 5-fluoro-2-nitrophenoxyl, 2-aminophenoxyl.

The term "cyclic ring or polycyclic system" means a system containing one or more rings containing from 3 to 14 carbon atoms, optionally containing heteroatoms selected from nitrogen, oxygen, sulfur, silicon, selenium, phosphorus. Specific examples of cyclic ring or polycyclic system are: thieno[3,2-b]thiophene, thiadiazole, benzothiophene, quinoxaline, pyridine.

Specific examples of disubstituted benzoheterodiazole compounds of general formula (I) useful for the object of the present invention are shown in Table 1.

TABLE 1

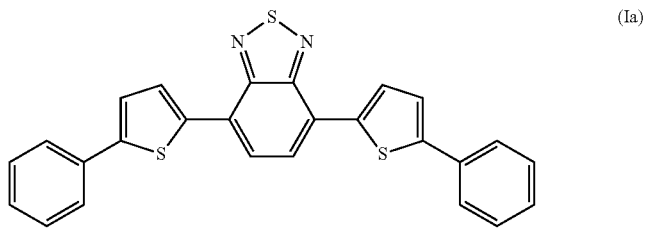

(Ia)

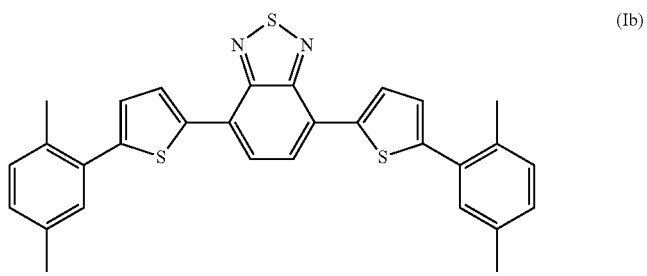

(Ib)

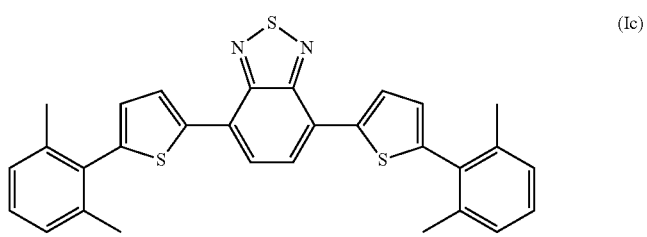

(Ic)

TABLE 1-continued
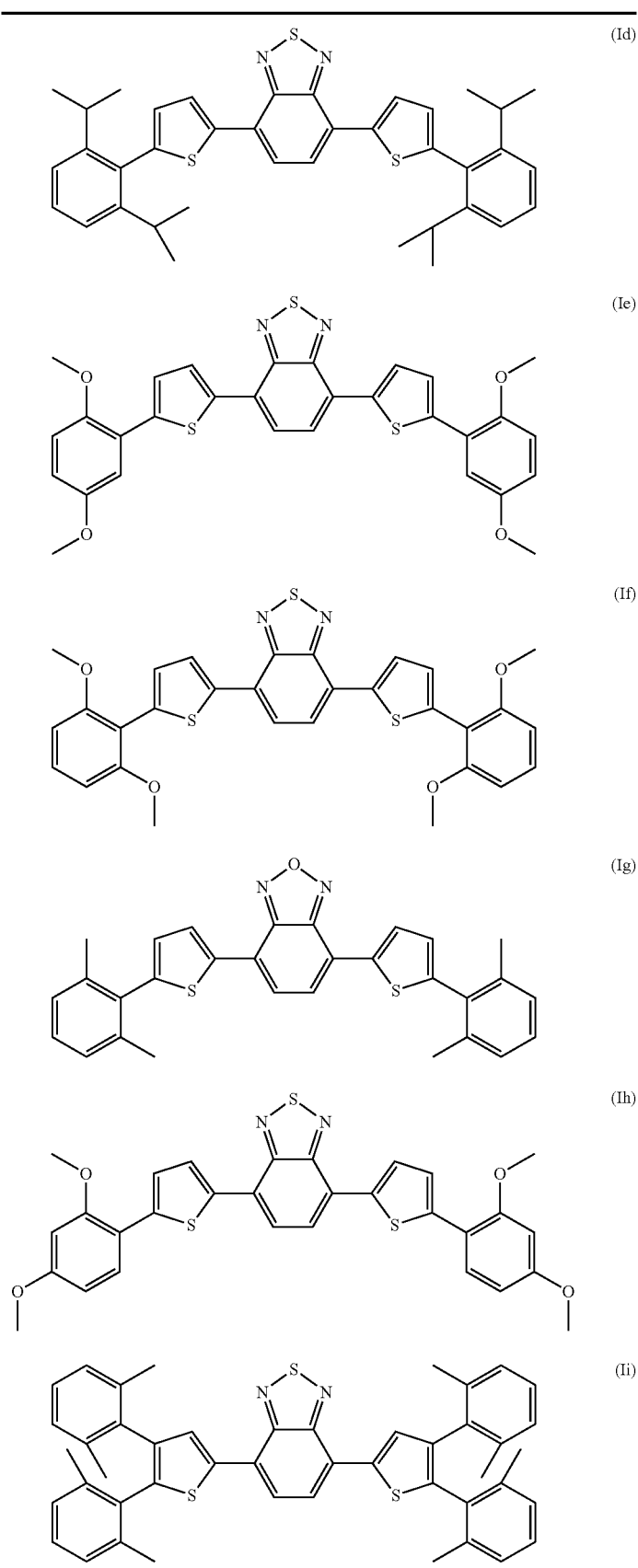

TABLE 1-continued

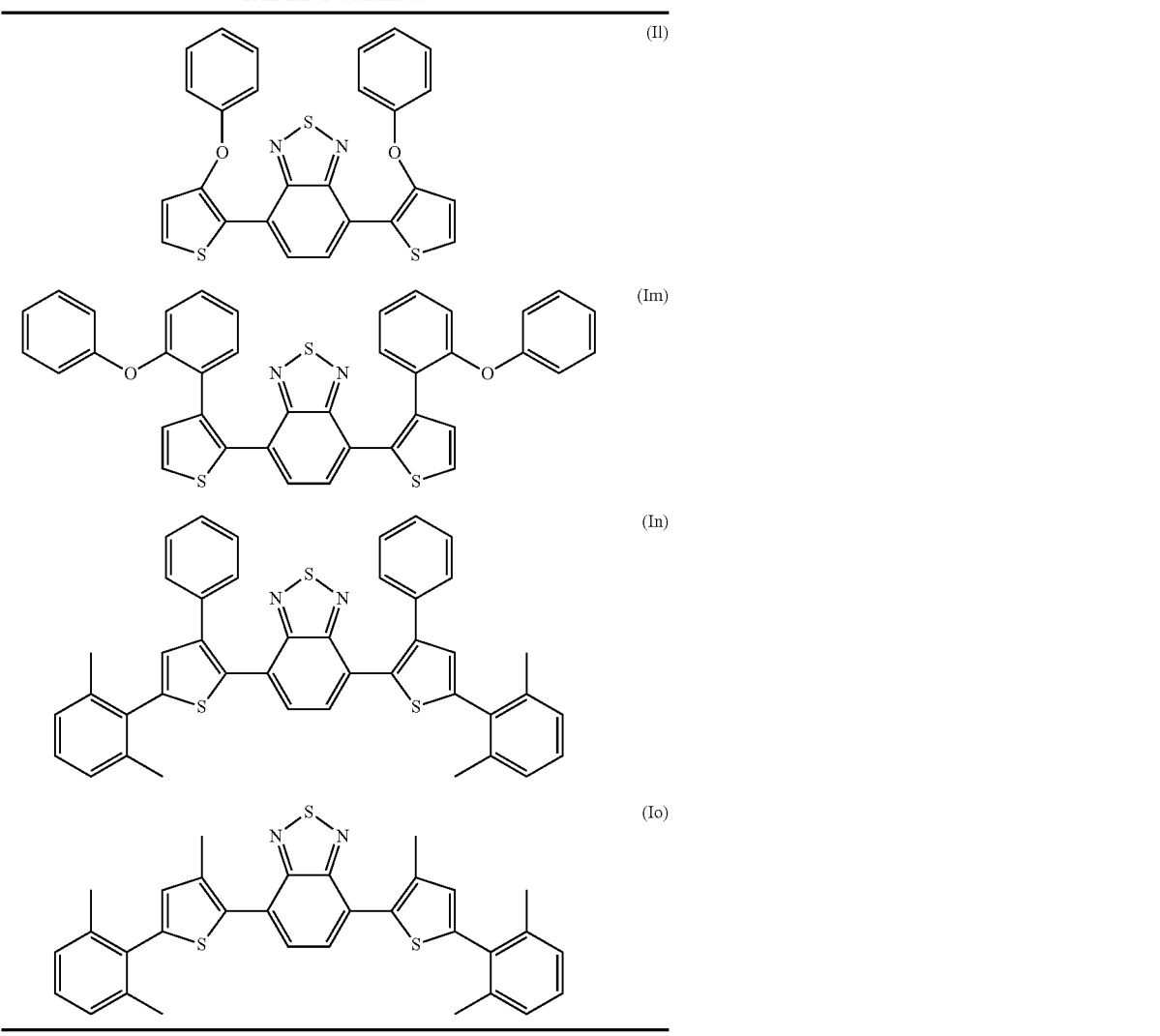

The said disubstituted benzoheterodiazole compound of general formula (I) can be obtained according to processes known in the art.

For example, in accordance with the first process, the said disubstituted benzoheterodiazole compound of general formula (I) can be obtained by means of the Suzuki reaction as shown in the following Scheme 1:

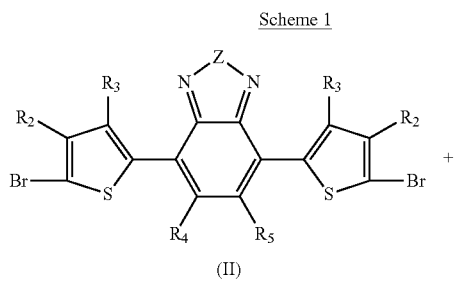

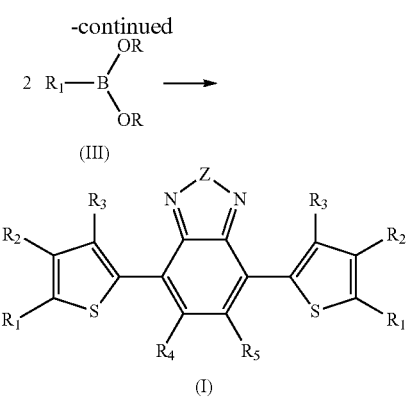

in which $R_1$, $R_2$, $R_3$, $R_4$ and $R_5$ have the same meanings as indicated above, R is a hydrogen atom, or can be selected from linear or branched $C_1$-$C_{10}$ alkyl groups, or from optionally substituted cycloalkyl groups, or the two R substituents can optionally be linked together to form a cyclic ring together with the other atoms to which they are linked as in the case of the pinacol esters of boronic acid or of the 1,3-propandiol esters of boronic acid.

For the purpose of the present invention, in the aforesaid Suzuki reaction, the said disubstituted dibrominated benzoheterodiazole compound of general formula (II) and the said boron compound of general formula (III) can be used in molar ratios ranging from 1:2 to 1:5, preferably ranging from 1:2 to 1:4.

Preferably, the aforesaid Suzuki reaction, is carried out in the presence of at least one catalyst containing palladium which can be selected from palladium compounds in oxidation state (0) or (II) such as, for example, palladium-tetrakistriphenylphosphine [Pd(PPh$_3$)$_4$], bis-triphenylphosphine palladium dichloride [PdCl$_2$(PPh$_3$)$_2$]. Preferably, the said disubstituted dibrominated benzoheterodiazole compound of general formula (II) and the said catalyst can be used in molar ratios ranging from 1:0.15 to 1:0.01, preferably ranging from 1:0.02 to 1:0.1.

Preferably, the aforesaid Suzuki reaction is carried out in the presence of at least a weak organic base which can be selected, for example, from carboxylates of alkali metals (e.g., sodium, potassium, caesium) or of alkaline-earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkali metals (e.g., lithium, sodium, potassium, caesium) or of alkaline-earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkali metal (e.g., lithium, sodium, potassium, caesium) or of alkaline earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; preferably potassium carbonate, sodium carbonate, caesium carbonate. The said base can be used as such, or in aqueous solution. Preferably, the said disubstituted dibrominated benzoheterodiazole of general formula (II) and the said weak organic base can be used in molar ratios ranging from 1:1 to 1:20, preferably ranging from 1:2 to 1:10.

Preferably, the aforesaid Suzuki reaction is carried out in the presence of at least one organic solvent which can be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; dipolar aprotic solvents such as, for example, N,N-dimethylformamide, N-methylpyrrolidone, dimethylsulfoxide; or mixtures thereof. The said organic solvent can also be used in a mixture with at least one alcohol such as, for example, methanol, ethanol, n-propanol, iso-propanol, or mixtures thereof.

Preferably, the aforesaid Suzuki reaction is carried out at a temperature ranging from 50° C. to 154° C., preferably ranging from 60° C. to 120° C.

Preferably, in the said Suzuki reaction the said disubstituted dibrominated benzoheterodiazole of general formula (II) can be used at a molar concentration ranging from 0.01 M to 2 M, preferably ranging from 0.02 M to 1 M.

The disubstituted dibrominated benzoheterodiazole compounds of general formula (II) can be obtained according to processes known in the art as described, for example, by Blouin N. et al. in "*Journal of the American Chemical Society*" (2008), Vol. 130, pg. 732-742, or by Zeng S. et al. in "*Dyes and Pigments*" (2012), Vol. 95, Issue 2, pg. 229-235, or are commercially available.

The boron compounds of general formula (III) are commercially available.

Alternatively, in accordance with a second process, the said disubstituted benzoheterodiazole compound of general formula (I) can be obtained by means of the Suzuki reaction as shown in the following Scheme 2:

Scheme 2

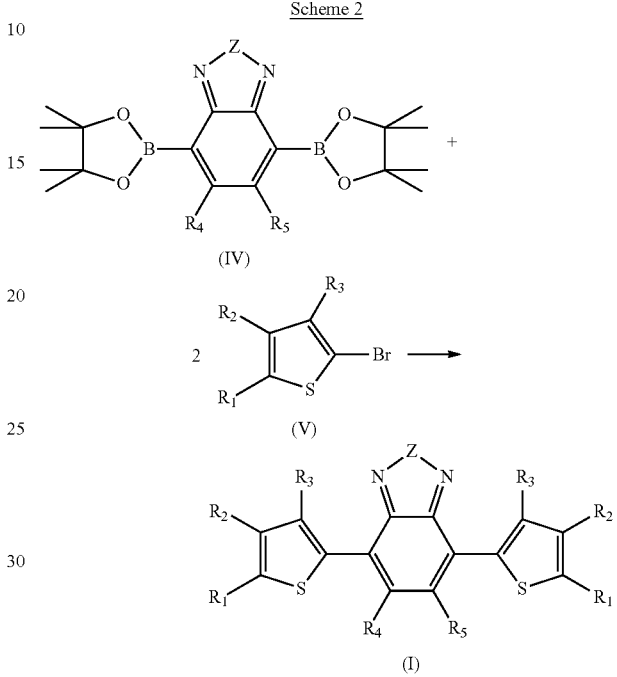

in which R$_1$, R$_2$, R$_3$, R$_4$ and R$_5$, have the same meanings as indicated above.

For the purpose of the present invention, in the aforesaid Suzuki reaction the said benzoheterodiazole diester of boronic acid of general formula (IV) and the said 2-bromothiophene of general formula (V) can be used in molar ratios ranging from 1:2 to 1:5, preferably ranging from 1:2 to 1:4.

Preferably, the aforesaid Suzuki reaction is carried out in the presence of at least one catalyst containing palladium which can be selected from palladium compounds in oxidation state (0) or (II) such as, for example, palladium-tetrakistriphenylphosphine [Pd(PPh$_3$)$_4$], bis-triphenylphosphine palladium dichloride [PdCl$_2$(PPh$_3$)$_2$]. Preferably, the said 2-bromothiophene of general formula (V) and the said catalyst can be used in molar ratios ranging from 1:0.15 to 1:0.01, preferably ranging from 1:0.02 to 1:0.1.

Preferably, the aforesaid Suzuki reaction is carried out in the presence of at least a weak organic base which can be selected, for example, from: carboxylates of alkali metals (e.g., sodium, potassium, caesium) or of alkaline-earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkali metals (e.g., lithium, sodium, potassium, caesium) or of alkaline-earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkali metal (e.g., lithium, sodium, potassium, caesium) or of alkaline earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; preferably potassium carbonate, sodium carbonate, caesium carbonate. The said base can be used as such, or in aqueous solution. Preferably, the said 2-bromothiophene of general formula (V) and the said weak organic base can be used in molar ratios ranging from 1:1 to 1:20, preferably ranging from 1:2 to 1:10.

Preferably, the aforesaid Suzuki reaction is carried out in the presence of at least one organic solvent which can be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; dipolar aprotic solvents such as, for example, N,N-dimethylformamide, N-methylpyrrolidone, dimethylsulfoxide; or mixtures thereof. The said organic solvent can also be used in a mixture with at least one alcohol such as, for example, methanol, ethanol, n-propanol, iso-propanol, or mixtures thereof.

Preferably, the aforesaid Suzuki reaction is carried out at a temperature ranging from 50° C. to 154° C., preferably ranging from 60° C. to 120° C.

Preferably, in said Suzuki reaction, the said 2-bromothiophene of general formula (V) can be used at a molar concentration ranging from 0.01 M to 2 M, preferably ranging from 0.02 M to 1 M.

The benzoheterodiazole diesters of boronic acid of general formula (IV) can be obtained according to processes known in the art as described, for example, by Zhang M. et al. in "*Journal of the American Chemical Society*" (2007), Vol. 129(12), pg. 3472-3473; or in the case in which $R_4=R_5=H$ are commercially available.

The 2-bromothiophene of general formula (V) can be obtained according to processes known in the art as described, for example, by Ohshimizu K. et al. in "*Macromolecules*" (2011), Vol. 44(4), pg. 719-727.

Alternatively, the said disubstituted benzoheterodiazole compound of general formula (I) can be obtained by a reaction between a dibrominated benzoheterodiazole compound and a 2-thienylboronic acid ester as described, for example, by Lee W. et al. in "*Tetrahedron*" (2013), Vol. 69, pg. 9175-9182, or by a reaction between a dibrominated dibenzoheterodiazole compound and a trialkyl-stannylthiophene as described, for example, in International Patent Application WO 2012/007834 in the name of the Applicant.

Alternatively, the said disubstituted benzoheterodiazole compound of general formula (I) can be obtained by direct palladium-catalysed arylation between 4,7-dibromobenzoheterodiazole and a thiophene as described, for example, in patent application WO 2013/021315 in the name of the Applicant.

A further object of the present invention is also the use of at least one disubstituted benzoheterodiazole compound of general formula (I) in the construction of luminescent solar concentrators (LSCs).

The disubstituted benzoheterodiazole compound of general formula (I) can be used in the said luminescent solar concentrator (LSC) in the following forms: dispersed in the polymer or in the glass, chemically bonded to the polymer or the glass, in solution, or in the form of gel.

For example, the lumincescent solar concentrator (LSC) can contain a transparent matrix, in which by the term transparent matrix is meant any transparent material used in the form of a support, binder or material in which at least one disubstituted benzoheterodiazole compound of general formula (I) is dispersed or incorporated. The material used for the matrix is transparent, as such, to the radiation of interest and in particular to radiation having frequencies within the effective spectrum of the photovoltaic device (or solar device) such as, for example, the photovoltaic cell (or solar cell) in which it is used. Suitable materials for the purpose of the present invention can therefore be selected from materials which are transparent at least to radiations having a wavelength ranging from 250 nm to 1100 nm.

The transparent matrix which can be used for the purpose of the present invention can, for example, be selected from polymer materials or vitreous materials. The said matrix is characterised by high transparency and high durability in relation to heat and light. Polymer materials which can advantageously be used for the purpose of the present invention are, for example, polymethylmethacrylate (PMMA), epoxy resins, silicone resins, polyalkylene terephthalates, polycarbonates, polystyrene, polypropylene. Vitreous materials which can advantageously be used for the purpose of the present invention are, for example, silicas.

In the case where the matrix is of the polymer type, the said at least one disubstituted benzoheterodiazole compound of general formula (I) can be dispersed in the polymer of the said matrix by, for example, dispersion in the molten state, with the subsequent formation of a sheet comprising the said polymer and the said at least one disubstiututed benzoheterodiazole compound of general formula (I), operating, for example, according to the technique known as "casting". Alternatively, the said at least one disubstituted benzoheterodiazole compound of general formula (I) and the polymer of said matrix can be dissolved in at least one solvent, obtaining a solution which is deposited on a sheet of the said polymer forming a film comprising the said at least one disubstituted benzoheterodiazole compound of general formula (I) and the said polymer, operating, for example, with the use of a "Doctor Blade" type film applicator: the said solvent is then allowed to evaporate.

In the case in which the matrix is of the vitreous type, the said at least one disubstituted benzoheterodiazole compound of general formula (I) can be dissolved in at least one solvent, obtaining a solution which is deposited on a sheet of the said matrix of vitreous type forming a film comprising the said at least one disubstituted benzoheterodiazole compound of general formula (I), operating, for example, with the use of a "Doctor Blade" type film applicator: the said solvent is then allowed to evaporate.

Yet another object of the present invention is a photovoltaic device (or solar device) comprising at least one photovoltaic cell (or solar cell) and at least one luminescent solar concentrator (LSC) including at least one disubstituted benzoheterodiazole compound of general formula (I).

The said photovoltaic device (or solar device) can, for example, be obtained by assembling the aforesaid luminescent solar concentrator with a photovoltaic cell (or solar cell).

In accordance with a preferred embodiment of the present invention the aforesaid solar concentrator can be made in the form of a transparent sheet obtained by dissolving the said at least one disubstituted benzoheterodiazole compound of general formula (I) and the polymer of the matrix of the polymer type in at least one solvent, obtaining a solution which is deposited on a sheet of the said polymer forming a film comprising the said at least one disubstiututed benzoheterodiazole compound of general formula (I) and the said polymer, operating, for example, with the use of a "Doctor Blade" type film applicator: the said solvent is then allowed to evaporate. In the said photovoltaic devices (or solar devices) the said sheets can then be coupled with a photovoltaic cell (or solar cell).

In accordance with a further preferred embodiment of the present invention, the aforesaid luminescent solar concentrator (LSC) can be realized in the form of a transparent sheet obtained according to the technique called casting by mixing at least one polymerizable monomer [for example, methylmethacrylate (MMA)] and at least one radical initiator [for example, azo-bis-iso-butyronitrile (AIBN)] obtaining a syrup of the pre-polymerized polymer of the matrix of the polymer type. To said syrup a solution is then added comprising at least one different radical initiator (for example, lauroyl peroxide), at least one polymerizable monomer, preferably the same monomer used to obtain the syrup, and the disubstituted benzoheterodiazole compound of general formula (I), obtaining a solution that is poured into a mold of suitable dimensions and polymerized: at the end of the polymerization, the sheet obtained is removed from the mold. In said photovoltaic devices (or solar devices), the sheet thus obtained can then be coupled to a photovoltaic cell (or solar cell).

For the purpose of a better understanding of the present invention and for its implementation a number of illustrative and non-limiting examples thereof are illustrated below.

The 4,7-di-(thien-2'-yl)-2,1,3-benzothiadiazole (DTB) was obtained as described in Example 1 of International Patent Application WO 2012/007834 in the name of the Applicant, the contents of which are incorporated here as a reference.

EXAMPLE 1

Synthesis of 4,7-bis[5-(phenyl)-2-thienyl]benzo[c]1,2,5-thiadiazole of Formula (Ia)

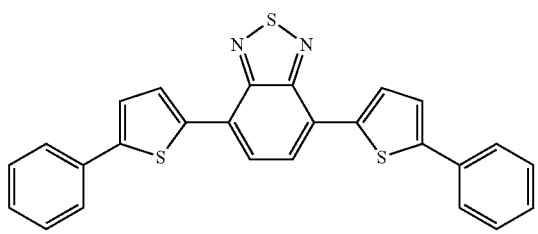 [SMILES: c1ccc(-c2ccc(-c3ccc(-c4ccc(-c5ccccc5)s4)c4nsnc34)s2)cc1]

(Ia)

In a 100 ml flask fitted with a magnetic stirrer, thermometer and condenser, under inert atmosphere, phenylboronic acid (Aldrich) (633.3 mg; 5.2 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (890 mg; 1.9 mmoles). After the air present had been removed by means of 3 vacuum/nitrogen cycles, palladium-tetrakistriphenylphosphine (Aldrich) (110 mg; 0.095 mmoles) was added, obtaining a reaction mixture which was heated to 95° C. and held at that temperature with stirring for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residual solvent was removed by distillation under reduced pressure. The residue obtained was purified by elution on a silica gel column [eluent: mixture n-heptane (Aldrich)/dichloromethane (Aldrich) in a ratio of 9/1 (v/v)], obtaining 0.6 g of 4,7-bis[5-(phenyl)-2-thienyl]benzo[c]1,2,5-thiadiazole of formula (Ia) [5-(Ph)$_2$DTB] (yield=70%).

EXAMPLE 2

Synthesis of 4,7-bis[5-(2,5-dimethylphenyl)-2-thienyl]benzo[c]1,2,5-thiadiazole of Formula (Ib)

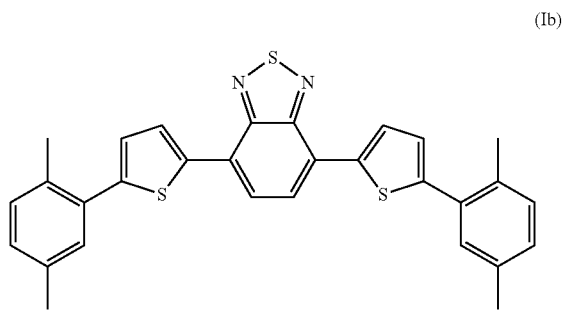

(Ib)

In a 100 ml flask fitted with a magnetic stirrer, thermometer and condenser, under inert atmosphere, 2,5-dimethylphenylboronic acid (Aldrich) (799 mg; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles, palladium-tetrakistriphenylphosphine (Aldrich) (110 mg; 0.095 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residual solvent was removed by distillation under reduced pressure. The residue obtained was purified by elution on a silica gel column [eluent: mixture n-heptane (Aldrich)/dichloromethane (Aldrich) in a ratio of 9/1 (v/v)], obtaining 0.6 g of 4,7-bis[5-(2,5-dimethylphenyl)-2-thienyl]benzo[c]1,2,5-thiadiazole of formula (Ib) {5-[2,5-(Me)$_2$Ph]$_2$DTB} (yield=60%).

EXAMPLE 3

Synthesis of 4,7-bis[5-(2,6-dimethylphenyl)-2-thienyl]benzo[c]1,2,5-thiadiazole of Formula (Ic)

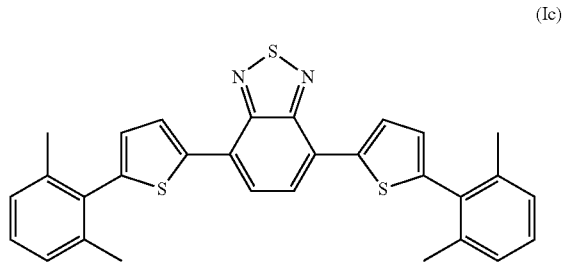

(Ic)

In a 100 ml flask fitted with a magnetic stirrer, thermometer and condenser, under inert atmosphere, 2,6-dimethylphenylboronic acid (Aldrich) (799 mg; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles, palladium-tetrakistriphenylphosphine (Aldrich) (110 mg; 0.095 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 1 g of 4,7-bis[5-(2,6-dimethylphenyl)-2-thienyl]benzo[c]1,2,5-thiadiazole of formula (Ic) {5-[2,6-(Me)$_2$Ph]$_2$DTB} (yield=94%).

EXAMPLE 4

Synthesis of 4,7-bis[5-(2,6-di-iso-propylphenyl)-2-thienyl]benzo[c]1,2,5-thiadiazole of Formula (Id)

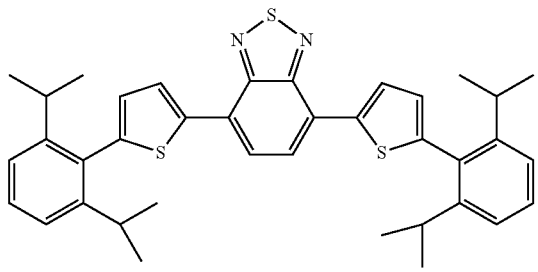 [SMILES: CC(C)c1cccc(C(C)C)c1-c1ccc(-c2ccc(-c3ccc(-c4c(C(C)C)cccc4C(C)C)s3)c3nsnc23)s1]

(Id)

In a 100 ml flask fitted with a magnetic stirrer, thermometer and condenser, under inert atmosphere, 2,6-di-iso-propylphenylboronic acid (Aldrich) (1 g; 4.85 mmoles) and caesium carbonate (Aldrich) (2.35 g; 7.2 mmoles) were added to a 0.1 m solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles bis-(triphenylphosphine)palladium dichloride (Aldrich) (86 mg; 0.12 mmoles) was added, obtaining a reaction mixture which was heated to 80° C. and held at that temperature, with stirring, for 14 hours. Then the reaction mixture was cooled to ambient temperature (25° C.) and filtered on a layer of celite: the residual solvent was removed by distillation under reduced pressure. The residue obtained was purified by elution on a silica gel column [eluent: mixture n-heptane (Aldrich)/dichloromethane (Aldrich) in a ratio of 9/1 (v/v)], obtaining 0.7 g of 4,7-bis[5-(2,6-di-iso-propylphenyl)-2-thienyl]benzo[c]1,2,5-thiadiazole of formula (Id) {5-[2,6-(i-Pr)$_2$Ph]$_2$DTB} (yield=93%).

EXAMPLE 5

Synthesis of 4,7-bis[5-(2,5-dimethoxyphenyl)-2-thienyl]benzo[c]1,2,5-thiadiazole of Formula (Ie)

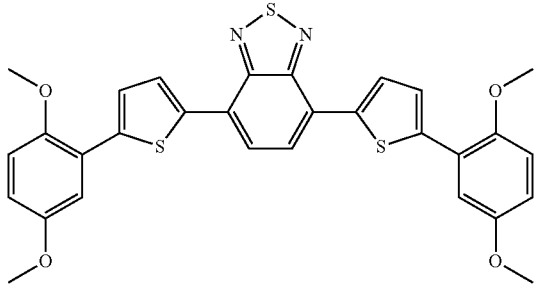 [SMILES: COc1ccc(OC)c(-c2ccc(-c3ccc(-c4ccc(-c5cc(OC)ccc5OC)s4)c4nsnc34)s2)c1]

(Ie)

In a 100 ml flask fitted with a magnetic stirrer, thermometer and condenser, under inert atmosphere, 2,5-dimethoxyphenylboronic acid (Aldrich) (1 g; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles, palladium-tetrakistriphenylphosphine (Aldrich) (110 mg; 0.095 mmoles) was added, obtaining a reaction mixture which was heated to 95° C. and held at that temperature with stirring for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich)/ethyl acetate (Aldrich) in a ratio of 8/1/1 (v/v/v)], obtaining 1 g of 4,7-bis[5-(2,5-dimethoxyphenyl)-2-thienyl]benzo[c]1,2,5-thiadiazole of formula (Ie) {5-[2,5-(MeO)$_2$Ph]$_2$DTB} (yield=82%).

EXAMPLE 6

Synthesis of 4,7-bis[5-(2,6-dimethoxyphenyl)-2-thienyl]benzo[c]1,2,5-thiadiazole of Formula (If)

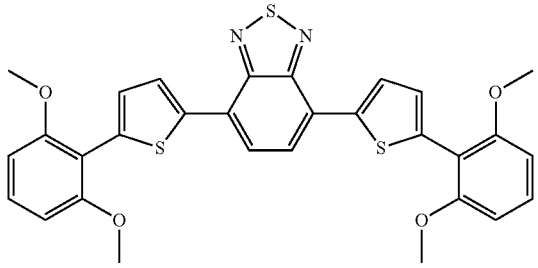 [SMILES: COc1cccc(OC)c1-c1ccc(-c2ccc(-c3ccc(-c4c(OC)cccc4OC)s3)c3nsnc23)s1]

(If)

In a 100 ml flask fitted with a magnetic stirrer, thermometer and condenser, under inert atmosphere, 2,6-dimethoxyphenylboronic acid (Aldrich) (1 g; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles, palladium-tetrakistri-phenylphosphine (Aldrich) (110 mg; 0.095 mmoles) was added, obtaining a reaction mixture which was heated to 95° C. and held at that temperature with stirring for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich)/ethyl acetate (Aldrich) in a ratio of 8/1/1 (v/v/v)], obtaining 1.1 g of 4,7-bis[5-(2,6-dimethoxyphenyl)-2-thienyl]benzo[c]1,2,5-thiadiazole of formula (If) {5-[2,6-(MeO)$_2$PH]$_2$DTB} (yield=88%).

EXAMPLE 7

Synthesis of 4,7-bis[5-(2,6-dimethylphenyl)-2-thienyl]benzo[c]1,2,5-oxadiazole of Formula (Ig)

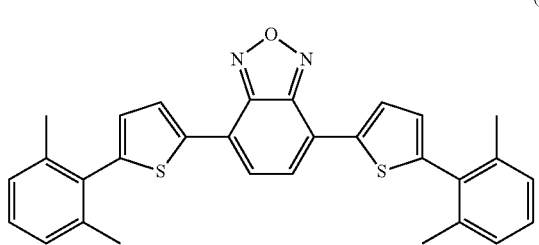

(Ig)

In a 100 ml flask fitted with a magnetic stirrer, thermometer and condenser, under inert atmosphere, 2,6-dimethylphenylboronic acid (Aldrich) (799 g; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzooxadiazole (928 mg; 2.1 mmoles) obtained as described by Blouin N. et al. in "*Journal of American Chemical Society*" (2008), Vol. 130, pg. 732-742. After the air present had been removed by means of 3 vacuum/nitrogen cycles, palladium-tetrakistri-phenylphosphine (Aldrich) (110 mg; 0.095 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 0.97 g of 4,7-bis[5-(2,6-dimethylphenyl)-2-thienyl]benzo[c]1,2,5-oxadiazole of formula (Ig) {5-[2,6-(Me)$_2$Ph]$_2$DTBO} (yield=94%).

EXAMPLE 8

Synthesis of 4,7-bis[5-(2,4-dimethoxyphenyl)-2-thienyl]benzo[c]1,2,5-thiadiazole of Formula (Ih)

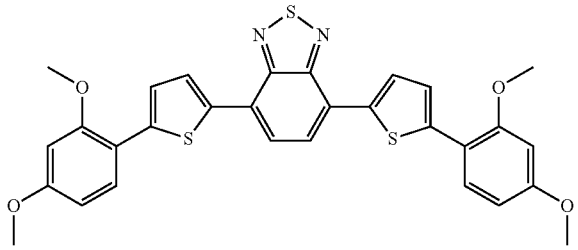 [SMILES: COc1ccc(-c2ccc(-c3ccc(-c4ccc(-c5ccc(OC)cc5OC)s4)c4nsnc34)s2)c(OC)c1]

(Ih)

In a 100 ml flask fitted with a magnetic stirrer, thermometer and condenser, under inert atmosphere, 2,4-dimethoxyphenylboronic acid (Aldrich) (1 g; 5.6 mmoles) and a 2.1 M aqueous solution of potassium carbonate (Aldrich) (2.5 g in 8.6 ml of water; 18.1 mmoles) were added to a 0.1 M solution in anhydrous 1,4-dioxane (Aldrich) of 4,7-bis(2-bromo-5-thienyl)-2,1,3-benzothiadiazole (Aldrich) (958 mg; 2.1 mmoles). After the air present had been removed by means of 3 vacuum/nitrogen cycles, palladium-tetrakistri-phenylphosphine (Aldrich) (110 mg; 0.095 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich)/ethyl acetate (Aldrich) in a ratio of 8/1/1 (v/v/v)], obtaining 1.1 g of 4,7-bis[5-(2,4-dimethoxyphenyl)-2-thienyl]benzo[c]1,2,5-thiadiazole of formula (Ih) {5-[2,4-(MeO)$_2$Ph]$_2$DTB} (yield=82%).

EXAMPLE 9

Synthesis of 2,3-bis(2,6-dimethylphenyl)thiophene of Formula (a)

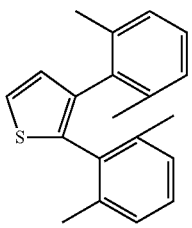

(a)

In a 100 ml flask fitted with a magnetic stirrer, under inert atmosphere, 2,6-dimethylphenylboronic acid (Aldrich) (1.98 g; 13.2 mmoles) and a 2.9 M aqueous solution of potassium carbonate (Aldrich) (6.0 g in 15 ml of water; 43.4 mmoles) were added to a 0.15 M solution in 1,4-dioxane (Aldrich) of 2,3-dibromothiophene (Aldrich) (1.27 g; 5.24 mmoles). After the air present had been removed by means of 3 vacuum/nitrogen cycles, palladium-tetrakistriphenylphosphine (Aldrich) (160 mg; 0.138 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: n-heptane (Aldrich)], obtaining 1.1 g of 2,3-bis(2,6-dimethylphenyl)thiophene of formula (a) (yield=72%).

EXAMPLE 10

Synthesis of 2,3-bis(2,6-dimethylphenyl)-5-bromo-thiophene of Formula (b)

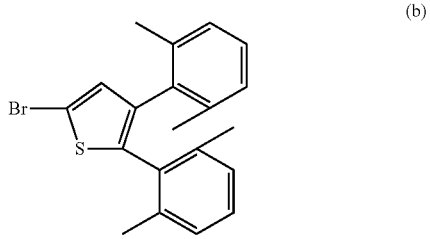

(b)

In a 100 ml flask fitted with a magnetic stirrer, themometer and condenser, under inert atmosphere, N-bromosuccinimide (Aldrich) (0.8 g, 4.52 mmoles) was added to a 0.1 M solution in anhydrous tetrahydrofuran (Aldrich) of 2,3-bis(2,6-dimethylphenyl)thiophene (1.1 g; 3.77 mmoles) obtained as described in Example 9. The reaction mixture was held at 20° C., with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)], obtaining 1.3 g of 2,3-bis(2,6-dimethylphenyl)-5-bromothiophene of formula (b) (yield=93%).

EXAMPLE 11

Synthesis of 4,7-bis[4,5-bis(2,6-dimethylphenyl)-2-thienyl]benzo[c]1,2,5-thiadiazole of Formula (Ii)

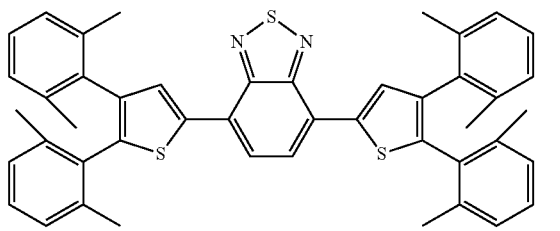 [SMILES: Cc1cccc(C)c1-c1cc(-c2ccc(-c3cc(-c4c(C)cccc4C)c(-c4c(C)cccc4C)s3)c3nsnc23)sc1-c1c(C)cccc1C]

(Ii)

In a 100 ml flask fitted with a magnetic stirrer, thermometer and condenser, under inert atmosphere, the pinacol ester of 4,7-benzothiadiazolediboronic diacid (Aldrich) (612 mg; 1.57 mmoles) and caesium carbonate (Aldrich) (3.65 g; 11.2 mmoles) were added to a 0.13 M solution in anhydrous 1,4-dioxane (Aldrich) of 2,3-bis(2,6-dimethylphenyl)-5-bromothiophene (1.3 g; 3.5 mmoles) obtained as described in Example 10. After the air present had been removed by means of 3 vacuum/nitrogen cycles, palladium-bis(triphenylphosphine)dichloride (Aldrich) (88.6 mg; 0.126 mmoles) was added, obtaining a reaction mixture which was heated to 85° C. and held at that temperature, with stirring, for 24 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 0.7 g of 4.7-bis[4,5-bis(2,6-dimethylphenyl)-2-thienyl]benzo[c]1,2,5-thiadiazole of formula (Ii) {4,5-[2,4-Me$_2$Ph]$_4$DTB} (yield=62%).

EXAMPLE 12

Synthesis of 3-phenoxythiophene of Formula (c)

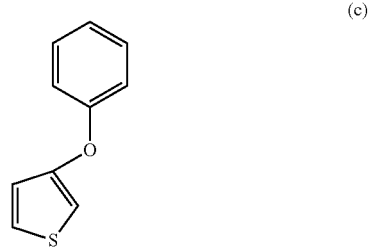

(c)

Copper iodide (I) (45.7 mg; 0.24 mmoles) (Aldrich), 2-picolinic acid (59.0 mg; 0.48 mmoles) (Aldrich), phenol (537 mg; 5.7 mmoles) (Aldrich) and potassium phosphate (2.0 g; 9.5 mmoles (Aldrich) were placed in a 50 ml Schlenk tube fitted with a screw stopper with a porous septum, under inert atmosphere. After the air present had been removed by means of 3 vacuum/nitrogen cycles, a 0.5 M solution in anhydrous dimethylsulfoxide (Aldrich) of 3-iodothiophene (1.0 g; 4.77 mmoles) (Aldrich) was added via a syringe and the tube was immersed in an oil bath preheated to 80° C.: the reaction mixture was held at that temperature, with stirring, for 24 hours. Then the reaction mixture was brought to 20° C., poured into distilled water (50 ml) and extracted with diethyl ether (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 98/2], obtaining 586.1 mg of 3-phenoxythiophene of formula (c) (yield=70%).

EXAMPLE 13

Synthesis of 3-phenoxy-2-bromothiophene e of Formula (d)

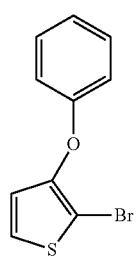

(d)

In a 100 ml flask fitted with a magnetic stirrer, under inert atmosphere, N-bromosuccinimide (Aldrich) (559.0 mg, 3.16 mmoles) was added to a 0.34 M solution in anhydrous tetrahydrofuran (Aldrich) of 3-phenoxythiophene (586.1 mg; 3.3 mmoles) obtained as described in Example 12. The reaction mixture was held in the dark at 20° C., with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)], obtaining 645 mg of 3-phenoxy-2-bromothiophene of formula (d) (yield=80%).

EXAMPLE 14

Synthesis of 4,7-bis[2-(3-phenoxy)-thienyl]benzo[c]1,2,5-thiadiazole of Formula (II)

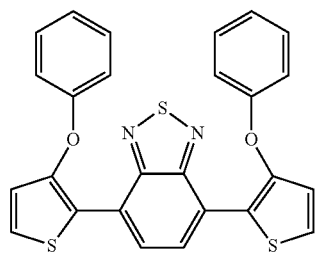 [SMILES: c1ccc(Oc2ccsc2-c2ccc(-c3sccc3Oc3ccccc3)c3nsnc23)cc1]

(II)

In a 100 ml flask fitted with a magnetic stirrer, themometer and condenser, under inert atmosphere, the pinacol ester of 4,7-benzothiadiazolediboronic diacid (Aldrich) (467 mg; 1.2 mmoles) and caesium carbonate (Aldrich) (2.82 g; 8.66 mmoles) were added to a 0.35 M solution in anhydrous 1,4-dioxane (Aldrich) of 3-phenoxy-2-bromothiophene (645 mg; 2.53 mmoles) obtained as described in Example 13. After the air present had been removed by means of 3 vacuum/nitrogen cycles, palladium-bis(triphenylphosphine) dichloride (Aldrich) (58.5 mg; 0.083 mmoles) was added, obtaining a reaction mixture which was heated to 85° C. and held at that temperature, with stirring, for 24 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 0.377 g of 4,7-bis[2-(3-phenoxy)-thienyl]benzo[c]1,2,5-thiadiazole of formula (II) {3-(PhO)₂DTB} (yield=65%).

EXAMPLE 15

Synthesis of 3-phenyl-2-bromothiophene of Formula (e)

(e)

In a 100 ml flask fitted with a magnetic stirrer, under inert atmosphere, N-bromosuccinimide (Aldrich) (2.1 g, 11.87 mmoles) was added to a 0.39 M solution in anhydrous tetrahydrofuran (Aldrich) of 3-phenylthiophene (Aldrich) (1.9 g; 11.87 mmoles) at 0° C. The reaction mixture was held at 20° C., with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)], obtaining 1.98 g of 3-phenyl-2-bromothiophene of formula (e) (yield=70%).

EXAMPLE 16

Synthesis of 4,7-bis[2-(3-phenyl)thienyl]benzo[c]1,2,5-thiadiazole of Formula (f)

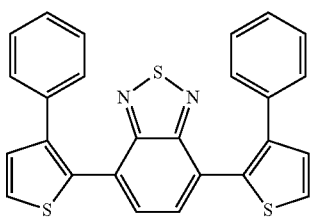

(f)

In a 100 ml flask fitted with a magnetic stirrer, themometer and condenser, under inert atmosphere, the pinacol ester of 4,7-benzothiadiazolediboronic diacid (Aldrich) (1.53 g; 3.94 mmoles) and caesium carbonate (Aldrich) (9.1 g; 27.94 mmoles) were added to a 0.34 M solution in anhydrous 1,4-dioxane (Aldrich) of 3-phenyl-2-bromothiophene (1.98 g; 8.28 mmoles) obtained as described in Example 15. After the air present had been removed by means of 3 vacuum/ nitrogen cycles, palladium-bis(triphenylphosphine)dichloride (Aldrich) (205.8 mg; 0.29 mmoles) was added, obtaining a reaction mixture which was heated to 85° C. and held at that temperature, with stirring, for 24 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 1.19 g of 4,7-bis[2-(3-phenyl)thienyl]benzo[c]1,2,5-thiadiazole of formula (f) (yield=67%).

EXAMPLE 17

Synthesis of 4,7-bis[2-(3-phenyl)-5-bromothienyl]benzo[c]1,2,5-thiadiazole of Formula (g)

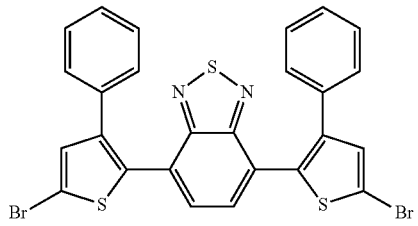

(g)

In a 100 ml flask fitted with a magnetic stirrer, under inert atmosphere, N-bromosuccinimide (Aldrich) (360 mg, 2.03 mmoles) (Aldrich) was added to a 0.1 M solution in anhydrous tetrahydrofuran (Aldrich) of 4,7-bis[2-(3-phenyl)-thienyl]benzo[c]1,2,5-thiadiazole (428.2 mg; 0.95 mmoles) obtained as described in Example 16. The reaction mixture was held at 20° C. in the dark, with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)], obtaining 520 mg of 4,7-bis[2-(3-phenyl)-5-bromothienyl]benzo[c]1,2,5-thiadiazole of formula (g) (yield=89.7%).

EXAMPLE 18

Synthesis of 4,7-bis[2-(3-phenyl)-5-(2,6-dimethylphenyl)-thienyl]benzo[c]1,2,5-thiadiazole of Formula (In)

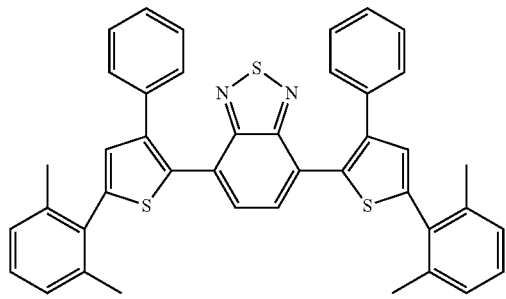

(In)

In a 100 ml flask fitted with a magnetic stirrer, themometer and condenser, under inert atmosphere, 2,6-dimethylphenylboronic acid (Aldrich) (345 mg; 2.3 mmoles) and a 2.13 M aqueous solution of potassium carbonate (Aldrich) (970 mg in 3.3 ml of water; 7.02 mmoles) were added to a 0.06 M solution in anhydrous 1,4-dioxane (Aldrich) of 4,7-bis[2-(3-phenyl)-5-bromothienyl]benzo[c]1,2,5-thiadiazole (520 mg; 0.85 mmoles) obtained as described in Example 17. After the air present had been removed by means of 3 vacuum/nitrogen cycles, palladium-tetrakistriphenylphosphine (Aldrich) (48.7 mg; 0.042 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich)/ethyl acetate (Aldrich) in a ratio of 9/1/0.5 (v/v/v)], obtaining 476.8 mg of 4,7-bis[2-(3-phenyl)-5-(2,6-dimethylphenyl)thienyl]benzo[c]1,2, 5-thiadiazole of formula (In) {[(3-Ph)-5-(2,6-Me$_2$Ph)]$_2$DTB}, (yield=85%).

EXAMPLE 19

Synthesis of 3-(2-phenoxyphenyl)thiophene of Formula (h)

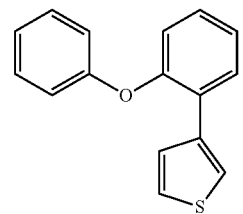

(h)

In a 100 ml flask fitted with a magnetic stirrer, under inert atmosphere, 2-phenoxyphenylboronic acid (Aldrich) (2.90 g; 13.56 mmoles) and a 2.1 M aqueous solution of potassium carbonate (Aldrich) (2.88 g in 9.93 ml of water; 20.86 mmoles) were added to a 0.15 M solution in 1,4-dioxane (Aldrich) of 3-bromothiophene (Aldrich) (1.7 g; 10.43 mmoles). After the air present had been removed by means of 3 vacuum/nitrogen cycles, palladium-tetrakistriphenylphosphine (Aldrich) (208 mg; 0.18 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: n-heptane (Aldrich)], obtaining 1.97 g of 3-(2-phenoxyphenyl)thiophene of formula (h) (yield=75%).

EXAMPLE 20

Synthesis of 3-(2-phenoxyphenyl)-2-bromothiophene of Formula (i)

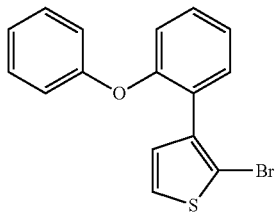

(i)

In a 100 ml flask fitted with a magnetic stirrer, under inert atmosphere, N-bromosuccinimide (Aldrich) (1.27 g, 7.19 mmoles) was added to a 0.1 M solution in anhydrous tetrahydrofuran (Aldrich) of 3-(2-phenoxyphenyl)thiophene (1.97 g; 7.82 mmoles) obtained as described in Example 19. The reaction mixture was kept in the dark at 20° C., with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)], obtaining 1.9 g of 3-(2-phenoxyphenyl)-2-bromothiophene of formula (I) (yield=80%).

EXAMPLE 21

Synthesis of 4,7-bis[2-(3-(2-phenoxy)phenyl)-thienyl]benzo[c]1,2,5-thiadiazole of Formula (Im)

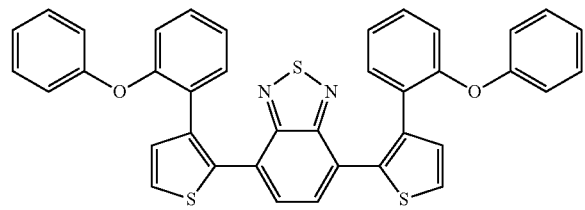 [SMILES: c1ccc(Oc2ccccc2-c2ccsc2-c2ccc(-c3sccc3-c3ccccc3Oc3ccccc3)c3nsnc23)cc1]

(Im)

In a 100 ml flask fitted with a magnetic stirrer, thermometer and condenser, under inert atmosphere, the pinacol ester of 4,7-benzothiadiazolediboronic diacid (Aldrich) (1.06 g; 2.73 mmoles) and caesium carbonate (Aldrich) (6.3 g; 19.5 mmoles) were added to a 0.35 M solution in anhydrous 1,4-dioxane (Aldrich) of 3-(2-phenoxyphenyl)-2-bromothiophene (1.9 g; 5.74 mmoles) obtained as described in Example 20. After the air present had been removed by means of 3 vacuum/nitrogen cycles, palladium-bis(triphenylphosphine)dichloride (Aldrich) (131.5 mg; 0.19 mmoles) was added, obtaining a reaction mixture which was heated to 85° C. and held at that temperature, with stirring, for 24 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich)/ethyl acetate in a ratio of 9/0.8/0.2 (v/v/v)], obtaining 1.13 g of 4,7-bis[2-(3-(2-phenoxy)phenyl)-thienyl]benzo[c] 1,2,5-thiadiazole of formula (Im) {3-(2-(PhO)-Ph)$_2$DTB} (yield=65%).

EXAMPLE 22

Synthesis of 4,7-bis[2-(3-methyl)thienyl]benzo[c]1,2,5-thiadiazole of Formula (I)

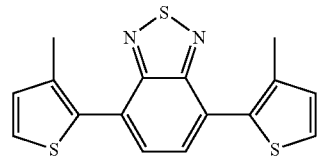

(l)

In a 100 ml flask fitted with a magnetic stirrer, thermometer and condenser, under inert atmosphere, the pinacol ester of 4,7-dibromobenzothiadiazole (Aldrich) (0.95 g; 3.23 mmoles) and a 2.17 M aqueous solution of potassium carbonate (Aldrich) (3.6 g; 26.08 mmoles in 12 ml of water) were added to a 0.17 M solution in 1,4-dioxane (Aldrich) of the pinacol ester of 3-methyl-2-thienylboronic acid (1.52 g; 6.8 mmoles) (Aldrich). After the air present had been removed by means of 3 vacuum/nitrogen cycles, palladium-tetrakistriphenylphosphine (Aldrich) (187 mg; 0.16 mmoles) was added, obtaining a reaction mixture which was heated to 95° C. and held at that temperature, with stirring, for 24 hours. The reaction mixture was then poured into distilled water (50 ml) and extracted with dichloromethane (Aldrich) (3×25 ml). The organic phase obtained was washed to neutral with distilled water (3×25 ml) and subsequently dried on sodium sulfate (Aldrich). The residue obtained was purified by elution on a silica gel column [eluent: mixture n-heptane (Aldrich)/dichloromethane (Aldrich) in a ratio of 9/0.5 (v/v)], obtaining 0.742 g of 4,7-bis[2-(3-(2-phenoxy)phenyl)-thienyl]benzo[c]1,2,5-thiadiazole of formula (I) (yield=70%) %).

EXAMPLE 23

Synthesis of 4,7-bis[2-(3-methyl-5-bromo)-thienyl]benzo[c]1,2,5-thiadiazole of Formula (m)

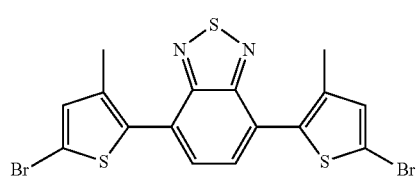

(m)

In a 100 ml flask fitted with a magnetic stirrer, under inert atmosphere, N-bromosuccinimide (Aldrich) (318.6 mg, 1.80 mmoles) was added to a 0.15 M solution in anhydrous tetrahydrofuran (Aldrich) of 4,7-bis[2-(3-methyl)-thienyl]benzo[c]1,2,5-thiadiazole (268.3 mg; 0.82 mmoles)

obtained as described in Example 22. The reaction mixture was held in the dark at 20° C., with stirring, for 14 hours. The reaction mixture was then poured into distilled water (50 ml) and extracted with dichloromethane (Aldrich) (3×25 ml). The organic phase obtained was washed with distilled water (2×25 ml) and subsequently dried on sodium sulfate (Aldrich). The residue obtained was purified by elution on a silica gel column [eluent: n-heptane (Aldrich)/ethyl acetate (Aldrich)=9/1 v/v], obtaining 318.8 mg of 4,7-bis[2-(3-methyl-5-bromo)-thienyl]benzo[c]1,2,5-thiadiazole of formula (m) (yield=80%).

EXAMPLE 24

Synthesis of 4,7-bis[2-(3-methyl)-5-(2,6-dimethylphenyl)-thienyl]benzo[c]1,2,5-thiadiazole of Formula (Io)

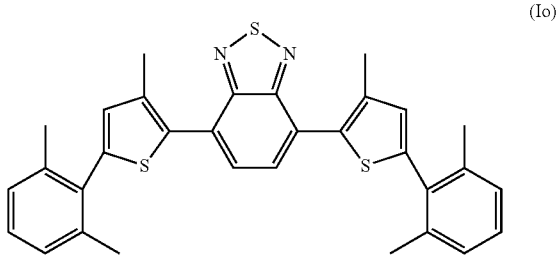 [SMILES: Cc1cc(-c2c(C)cccc2C)sc1-c1ccc(-c2sc(-c3c(C)cccc3C)cc2C)c2nsnc12]

(Io)

In a 100 ml flask fitted with a magnetic stirrer, thermometer and condenser, under inert atmosphere, 2,6-dimethylphenylboronic acid (Aldrich) (267.3 mg; 1.78 mmoles) and a 2.2 M aqueous solution of potassium carbonate (Aldrich) (751.6 mg in 2.48 ml of water; 5.45 mmoles) were added to a 0.07 M solution in anhydrous 1,4-dioxane (Aldrich) of 4,7-bis[2-(3-methyl-5-bromo)-thienyl]benzo[c]1,2,5-thiadiazole (318.8 mg; 0.56 mmoles) obtained as described in Example 23. After the air present had been removed by means of 3 vacuum/nitrogen cycles, palladium-tetrakistriphenylphosphine (Aldrich) (36.6 mg; 0.032 mmoles) was added, obtaining a reaction mixture which was heated to 95° C. and held at that temperature, with stirring, for 14 hours. The reaction mixture was then poured into distilled water (50 ml) and extracted with dichloromethane (Aldrich) (3×25 ml). The organic phase obtained was washed to neutral with distilled water (3×ml) and subsequently dried on sodium sulfate (Aldrich). The residue obtained was purified by elution on a silica gel column [eluent: mixture n-heptane (Aldrich)/dichloromethane (Aldrich) in a ratio of 9/1 (v/v)], obtaining 298.8 mg of 4,7-bis[2-(3-methyl)-5-(2,6-dimethylphenyl)-thienyl]benzo[c]1,2,5-thiadiazole of formula (Io) {(3-Me)$_2$-5-(2,6-Me$_2$Ph)$_2$DTB} (yield=85%).

EXAMPLE 25 (COMPARATIVE)

6 g of Altuglas VSUVT 100 (PMMA) polymethylmethacrylate and 49.5 mg of 4,7-di-(thien-2'-yl)-2,1,3-benzothiadiazole (DTB) were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of a yellow colour provided by the film, whose thickness was ranging from 100 µm to 50 µm (Sheet 1).

An IXYS-KXOB22-12 photovoltaic cell with a surface area of 1.2 cm$^2$ was then applied to one of the edges of the polymer sheet.

The main surface of the photovoltaic cell [that coated with the thin film containing the 4,7-di-(thien-2'-yl)-2,1,3-benzothiadiazole (DTB)] was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 5.69 mW in the absence of edge effects (FIG. 1).

Figure 2:
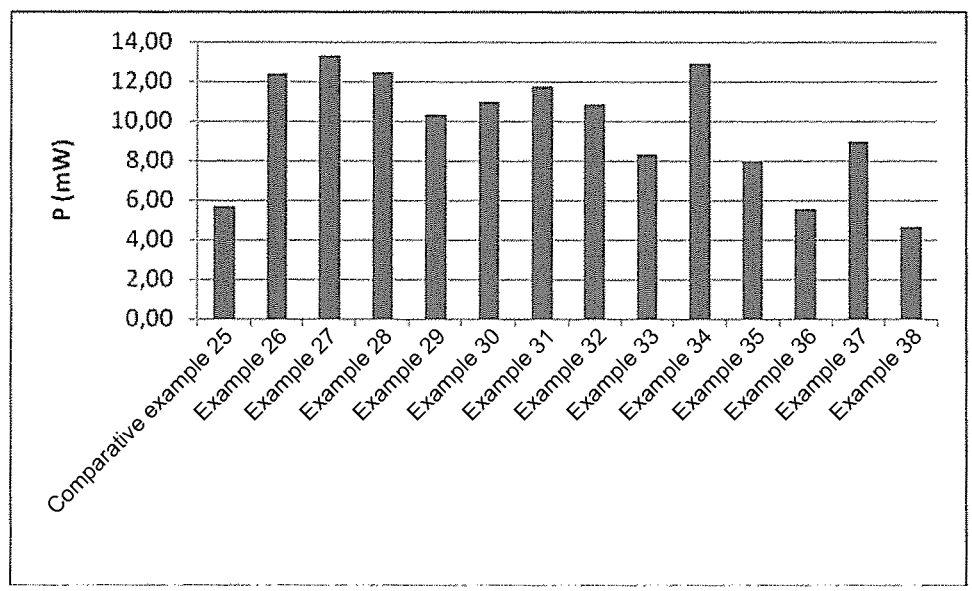

FIG. 2 shows the obtained value of the power (P) generated expressed in mW (shown in the ordinate) (the example number is shown in the abscissa).

EXAMPLE 26

6 g of Altuglas VSUVT 100 (PMMA) polymethylmethacrylate and 40.3 mg of 4,7-bis[5-phenyl-2-thienyl]benzo[c]1,2,5-thiadiazole of formula (Ia) [5-(Ph)$_2$DTB] obtained as described in Example 1, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of a red colour provided by the film, whose thickness was ranging from 100 µm to 50 µm (Sheet 2).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 12.36 mW in the absence of edge effects (FIG. 1).

FIG. 2 shows the obtained value of the power (P) generated expressed in mW (shown in the ordinate) (the example number is shown in the abscissa).

EXAMPLE 27

6 g of Altuglas VSUVT 100 (PMMA) polymethylmethacrylate and 101.5 mg of 4,7-bis[5-(2,5-dimethylphenyl)-2-thienyl]benzo[c]1,2,5-thiadiazole {5-[2,5-(Me)$_2$Ph]$_2$DTB} of formula (Ib) obtained as described in Example 2, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 3).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 13.30 mW in the absence of edge effects (FIG. 1).

FIG. 2 shows the obtained value of the power (P) generated expressed in mW (shown in the ordinate) (the example number is shown in the abscissa).

EXAMPLE 28

6 g of Altuglas VSUVT 100 (PMMA) polymethylmethacrylate and 101.5 mg of 4,7-bis[5-(2,6-dimethylphenyl)-2-thienyl]benzo[c]1,2,5-thiadiazole {5-[2,6-(Me)$_2$Ph]$_2$DTB} of formula (Ic) obtained as described in Example 3, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 4).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 12.42 mW in the absence of edge effects (FIG. 1).

FIG. 2 shows the obtained value of the power (P) generated expressed in mW (shown in the ordinate) (the example number is shown in the abscissa).

EXAMPLE 29

6 g of Altuglas VSUVT 100 (PMMA) polymethylmethacrylate and 111.6 mg of 4,7-bis[5-(2,6-di-iso-propylphenyl)-2-thienyl]benzo[c]1,2,5-thiadiazole of formula (Id) {5-[2,6-(i-Pr)$_2$Ph]$_2$DTB} obtained as described in Example 4, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 5).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 10.30 mW in the absence of edge effects (FIG. 1).

FIG. 2 shows the obtained value of the power (P) generated expressed in mW (shown in the ordinate) (the example number is shown in the abscissa).

EXAMPLE 30

6 g of Altuglas VSUVT 100 (PMMA) polymethylmethacrylate and 100.4 mg of 4,7-bis[5-(2,5-dimethoxyphenyl)-2-thienyl]benzo[c]1,2,5-thiadiazole of formula (Ie) {5-[2,5-(MeO)$_2$Ph]$_2$DTB} obtained as described in Example 5, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 6).

An IXYS-KXOB22-12 photovoltaic cell with a surface area of 1.2 cm² was then applied to one of the edges of the polymer sheet.

The main surface of the photovoltaic cell (that coated with the thin film) was then illuminated using a light source having a power of 1 sun (1000 W/m²) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 10.95 mW in the absence of edge effects (FIG. 1).

FIG. 2 shows the obtained value of the power (P) generated expressed in mW (shown in the ordinate) (the example number is shown in the abscissa).

EXAMPLE 31

6 g of Altuglas VSUVT 100 (PMMA) polymethylmethacrylate and 118.4 mg of 4,7-bis[5-(2,6-dimethoxyphenyl)-2-thienyl]benzo[c]1,2,5-thiadiazole of formula (If) {5-[2,6-(MeO)$_2$Ph]$_2$DTB} obtained as described in Example 6, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 7).

An IXYS-KXOB22-12 photovoltaic cell with a surface area of 1.2 cm² was then applied to one of the edges of the polymer sheet.

The main surface of the photovoltaic cell (that coated with the thin film) was then illuminated using a light source having a power of 1 sun (1000 W/m²) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 11.76 mW in the absence of edge effects (FIG. 1).

FIG. 2 shows the obtained value of the power (P) generated expressed in mW (shown in the ordinate) (the example number is shown in the abscissa).

EXAMPLE 32

6 g of Altuglas VSUVT 100 (PMMA) polymethylmethacrylate and 102 mg of 4,7-bis[5-(2,6-dimethylphenyl)-2-thienyl]benzo[c]1,2,5-oxadiazole of formula (Ig) {5-[2,6-(Me)$_2$Ph]$_2$DTBO} obtained as described in Example 7, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 8).

An IXYS-KXOB22-12 photovoltaic cell with a surface area of 1.2 cm² was then applied to one of the edges of the polymer sheet.

The main surface of the photovoltaic cell (that coated with the thin film) was then illuminated using a light source having a power of 1 sun (1000 W/m²) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 10.83 mW in the absence of edge effects (FIG. 1).

FIG. 2 shows the obtained value of the power (P) generated expressed in mW (shown in the ordinate) (the example number is shown in the abscissa).

EXAMPLE 33

6 g of Altuglas VSUVT 100 (PMMA) polymethylmethacrylate and 103 mg of 4,7-bis[5-(2,4-dimethoxyphenyl)-2-thienyl]benzo[c]1,2,5-thiadiazole of formula (Ih) {5-[2,4-(MeO)$_2$Ph]$_2$DTB} obtained as described in Example 8, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 9).

An IXYS-KXOB22-12 photovoltaic cell with a surface area of 1.2 cm² was then applied to one of the edges of the polymer sheet.

The main surface of the photovoltaic cell (that coated with the thin film) was then illuminated using a light source having a power of 1 sun (1000 W/m²) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 8.32 mW in the absence of edge effects (FIG. 1).

FIG. 2 shows the obtained value of the power (P) generated expressed in mW (shown in the ordinate) (the example number is shown in the abscissa).

EXAMPLE 34

6 g of Altuglas VSUVT 100 (PMMA) polymethylmethacrylate and 129 mg of 4,7-bis[4,5-bis(2,6-dimethylphenyl)-2-thienyl]benzo[c]1,2,5-thiadiazole of formula (Ii) {4,5-[2,4-Me$_2$Ph]$_4$DTB} obtained as described in Example 11, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 10).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 12.89 mW in the absence of edge effects (FIG. 1).

FIG. 2 shows the obtained value of the power (P) generated expressed in mW (shown in the ordinate) (the example number is shown in the abscissa).

EXAMPLE 35

6 g of Altuglas VSUVT 100 (PMMA) polymethylmethacrylate and 81.6 mg of 4,7-bis[2-(3-phenoxy)-thienyl]benzo[c]1,2,5-thiadiazole of formula (II) {3-(PhO)$_2$DTB} obtained as described in Example 14, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 11).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 7.92 mW in the absence of edge effects (FIG. 1).

FIG. 2 shows the obtained value of the power (P) generated expressed in mW (shown in the ordinate) (the example number is shown in the abscissa).

EXAMPLE 36

6 g of Altuglas VSUVT 100 (PMMA) polymethylmethacrylate and 110.9 mg of 4,7-bis[2-(3-(2-phenoxy)phenyl)-thienyl]benzo[c]1,2,5-thiadiazole of formula (Im) {3-(2-(PhO)-Ph)$_2$DTB} obtained as described in Example 21, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 12).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 5.57 mW in the absence of edge effects (FIG. 1).

FIG. 2 shows the obtained value of the power (P) generated expressed in mW (shown in the ordinate) (the example number is shown in the abscissa).

EXAMPLE 37

6 g of Altuglas VSUVT 100 (PMMA) polymethylmethacrylate and 120.0 mg of 4,7-bis[2-(3-phenyl)-5-(2,6-dimethylphenyl)-thienyl]benzo[c]1,2,5-thiadiazole of formula (In) {[(3-Ph)-5-(2,6-Me$_2$Ph)]$_2$DTB} obtained as described in Example 18, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 13).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 8.99 mW in the absence of edge effects (FIG. 1).

FIG. 2 shows the obtained value of the power (P) generated expressed in mW (shown in the ordinate) (the example number is shown in the abscissa).

EXAMPLE 38

6 g of Altuglas VSUVT 100 (PMMA) polymethylmethacrylate and 97.8 mg of 4,7-bis[2-(3-methyl)-5-(2,6-dimethylphenyl)-thienyl]benzo[c]1,2,5-thiadiazole of formula (Io) {(3-Me)$_2$-5-(2,6-Me$_2$Ph)$_2$DTB} obtained as described in Example 24, were dissolved in 30 ml of 1,2-dichlorobenzene (Aldrich). The solution obtained was then uniformly deposited on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour provided by the film, whose thickness was ranging from 100 μm to 50 μm (Sheet 14).

An IXYS-KXOB22-12 photovoltaic cell with a surface area of 1.2 cm$^2$ was then applied to one of the edges of the polymer sheet.

The main surface of the photovoltaic cell (that coated with the thin film) was then illuminated using a light source having a power of 1 sun (1000 W/m$^2$) and the electrical power generated through the effect of the illumination was then measured.

Measurements of power (P) were then made by illuminating a portion of sheet of dimensions 100 mm×90 mm at an increasing distance (d) from the edge to which the photovoltaic cell was attached. These measurements at a varying distance from the photovoltaic cell make it possible to quantify the contributions of wave guide, edge, diffusion and autoabsorption effects.

FIG. 1 shows the graph for the power (P) generated expressed in mW (shown in the ordinate) as a function of distance (d) from the edge to which the photovoltaic cell was attached, expressed in cm (shown in the abscissa).

It will be seen how the mean power generated was 4.64 mW in the absence of edge effects (FIG. 1).

FIG. 2 shows the obtained value of the power (P) generated expressed in mW (shown in the ordinate) (the example number is shown in the abscissa).

EXAMPLE 39 (COMPARATIVE) 40-42 (INVENTION)

400 ml of methyl methacrylate (MMA) (Aldrich 99%), previously distilled, were heated to 80° C., in 2 hours, under magnetic agitation, in a 1 liter flask. Subsequently, 40 mg of azo-bis-iso-butyronitrile (AIBN) (Aldrich 98%) dissolved in 40 ml of methyl methacrylate (MMA) (Aldrich 99%), previously distilled, were added: the mixture obtained was heated, under magnetic agitation, to 94° C., in 1 hour, left at said temperature for 2 minutes, and subsequently cooled in an ice bath, obtaining a syrup of pre-polymerized polymethyl-methacrylate (PMMA).

400 ml of the pre-polymerized syrup obtained as described above were loaded into a 1 liter flask, and 25 mg of lauroyl peroxide (Acros 99%) dissolved in methyl methacrylate (MMA) (Aldrich 99%), previously distilled, were added, and a quantity of 4,7-di(thien-2'-il-2,1,3-benzothiadiazole (DTB) [in Example 39 (comparative)] or of disubstituted benzoheterodiazole compound of general formula (I), obtained as described in the examples reported above [in Examples 40 (invention): compound (Ic) of Example 3; in Example 41 (invention): compound (Id) of Example 4; and in Example 42 (invention): compound (Ii) of Example 11], such that the molar percentage of said 4,7-di(thien-2'-il)-2,1,3-benzothiadiazole (DTB) or of said disubstituted benzoheterodiazole compound of general formula (I), with respect to methyl methacrylate (MMA) is equal to 0.3. The mixture obtained was degassed, under magnetic agitation, under a vacuum of 10 mm mercury (Hg), for 45 minutes, at ambient temperature (25° C.), obtaining a solution that was poured into the mold described below.

Said mold was formed by two sheets of glass with dimensions 40×40 cm and thickness 6 mm-10 mm, separated by polyvinylchloride (PVC) gaskets (10 cm diameter). Said sheets of glass were mounted between jaws and pressed together until the space between the two sheets was about 6 mm. After closing the opening through which the aforementioned solution was poured with the gasket, the mold was immersed in a water bath, at 55° C., for 48 hours, and then placed in the stove and heated to 95° C. for 24 hours. Subsequently, the mold was cooled to ambient temperature (25° C.), the jaws and the gasket were removed, the glass sheets of the mold were separated, and the sheet of polymethylmethacrylate (PMMA) obtained was collected. The sheet of polymethyl-methacrylate (PMMA) was then cut into sheets with dimensions 30×7.5 cm in order to carry out the aging tests reported below.

The different sheets obtained as described above were subjected to accelerated aging in an ATLAS XenoTest Beta+, equipped with a Xenon lamp cooled in air and with Xenochrome 300 filter, operating in accordance with standard DIN EN ISO 4892-2-A1 2003-11.

Periodically, the sheets were removed and subjected to UV-visible spectroscopy.

The ultraviolet and visible absorption spectra (190 nm-850 nm) were recorded with a double beam UV-Vis-NIR spectrophotometer and double monochromator, with a passband of 2.0 nm and step of 1 nm.

Therefore, through said UV-visible spectroscopy, the quantity of fluorescent compound present on the sheets was determined by measuring the characteristic absorbance of each fluorescent compound, subject to calibration through reference sheets containing known quantities of fluorescent compound dispersed in the polymeric matrix itself.

In the sheets subject to accelerated aging the spectrophotometry of UV-vis absorption allowed the absorbance reduction in the visible region to be monitored by measuring the relative absorbance percentage (A %) defined as (At)/(A0), i.e. the ratio of absorbance at time t (At) to absorbance at time 0 (A0): in particular, the absorbance values (At) and (A0) are the mean of the absorbance values measured on each sheet in various points, at time t and at time zero, respectively.

Table 2 reports the relative absorbance percentage values (A %) [(At)/(A0)] according to the aging time [t (h)].

TABLE 2

| | (A %) [(At)/(A0)] | | | |
|---|---|---|---|---|
| t (h) | Example 39 (DTB) | Example 40 [compound (Ic)] | Example 41 [compound (Id)] | Example 42 [compound (Ii)] |
| 0 | 100 | 100 | 100 | 100 |
| 300 | 84 | 96 | 93 | 90 |
| 500 | 66 | 88 | 89 | 85 |
| 900 | — | — | — | 76 |
| 1000 | 51 | 77 | 80 | — |
| 1500 | 32 | — | — | 63 |
| 1800 | 17 | — | — | — |
| 2000 | — | 61 | 65 | — |

From the data reported in Table 2 it can be inferred that the fluorescent compounds in accordance with the present invention (Examples 40-42) have a higher relative absorbance percentage (A %) even after a number of hours of aging, with respect to 4,7-di(thien-2'-yl)-2,1,3-benzothiadiazole (DTB) known in the art [Example 39 (comparative)].

The invention claimed is:

1. Luminescent solar concentrator comprising at least one disubstituted benzoheterodiazole compound of general formula (I):

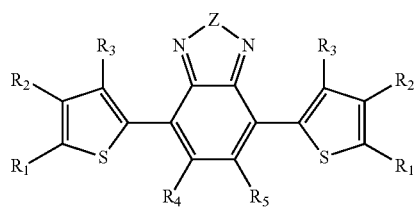

(I)

in which:
Z represents a sulfur atom, an oxygen atom, a selenium atom, or an $NR_6$ group in which $R_6$ is selected from:
i) linear or branched $C_1$-$C_{20}$ alkyl groups, or ii) optionally substituted-aryl groups;
$R_1$, $R_2$ and $R_3$, which are the same or different, represent a hydrogen atom, except $R_1$, $R_2$ and $R_3$ cannot all represent hydrogen, or are selected from: i) linear or branched $C_1$-$C_{20}$ alkyl groups optionally containing heteroatoms, ii) optionally substituted cycloalkyl groups, iii) optionally substituted aryl groups, iv) optionally substituted linear or branched $C_1$-$C_{20}$ alkoxyl groups, v) optionally substituted phenoxyl groups, or vi) —$COOR_7$ groups or —$OCOR_7$ groups in which $R_7$ is selected from linear or branched $C_1$-$C_{20}$-alkyl groups, or $R_7$ is a cyano group, and provided that when the substituents $R_1$ represents a hydrogen atom, at least one of the substituents $R_2$ and $R_3$ represents an optionally substituted phenoxyl group;
$R_1$ and $R_2$ can optionally be linked together so as to form, together with carbon atoms to which they are linked, a saturated, unsaturated or aromatic cyclic ring, or a polycyclic system containing from 3 to 14 carbon atoms, the cyclic ring or polycyclic system optionally containing one or more heteroatoms;
$R_2$ and $R_3$ can optionally be linked together so as to form, together with carbon atoms to which they are linked, a saturated, unsaturated or aromatic cyclic ring, or a polycyclic system containing from 3 to 14 carbon atoms, the cyclic ring or polycyclic system optionally containing one or more heteroatoms;
$R_4$ and $R_5$, which are the same or different, represent a hydrogen atom, or are selected from: i) linear or branched $C_1$-$C_{20}$ alkyl groups optionally containing heteroatoms, ii) optionally substituted cycloalkyl groups, iii) optionally substituted aryl groups, iv) optionally substituted linear or branched $C_1$-$C_{20}$ alkoxyl groups, or v) —$COOR_7$ groups or —$OCOR_7$ groups in which $R_7$ is selected from linear or branched $C_1$-$C_{20}$ alkyl groups, or $R_7$ is a cyano group;
$R_4$ and $R_5$ can optionally be linked together so as to form, together with carbon atoms to which they are linked, a saturated, unsaturated, or aromatic cyclic ring, or a polycyclic system containing from 3 to 14 carbon atoms, the cyclic ring or polycyclic system optionally containing one or more heteroatoms.

2. Luminescent solar concentrator according to claim 1, wherein in said general formula (I):
Z represents a sulfur atom or an oxygen atom;
$R_1$ are selected from optionally substituted aryl groups or optionally substituted phenoxyl groups;
$R_2$ and $R_3$, which are the same or different, represent a hydrogen atom, or are selected from: i) linear or branched $C_1$-$C_{20}$ alkyl groups, ii) optionally substituted aryl groups, or iii) optionally substituted phenoxyl groups;
$R_4$ and $R_5$, which are the same, represent a hydrogen atom.

3. Photovoltaic device comprising at least one photovoltaic cell, and at least one luminescent solar concentrator including at least a disubstituted benzoheterodiazole compound of general formula (I) according to claim 1.

4. Luminescent solar concentrator comprising at least one disubstituted benzoheterodiazole compound of general formula (I):

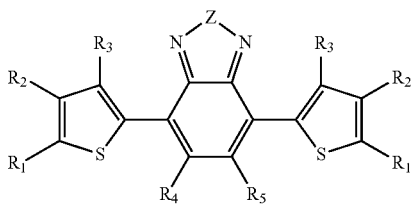

(I)

in which:
- Z represents a sulfur atom, an oxygen atom, a selenium atom, or an $NR_6$ group in which $R_6$ is selected from: i) linear or branched $C_1$-$C_8$ alkyl groups, or ii) optionally substituted-aryl groups;
- $R_1$, $R_2$ and $R_3$, which are the same or different, represent a hydrogen atom, except $R_1$, $R_2$ and $R_3$ cannot all represent hydrogen, or are selected from: i) linear or branched $C_1$-$C_8$ alkyl groups optionally containing heteroatoms, ii) optionally substituted cycloalkyl groups, iii) optionally substituted aryl groups, iv) optionally substituted linear or branched $C_1$-$C_8$ alkoxyl groups, v) optionally substituted phenoxyl groups, or vi) —$COOR_7$ groups or —$OCOR_7$ groups in which $R_7$ is selected from linear or branched $C_1$-$C_8$-alkyl groups, or $R_7$ is a cyano group, and provided that when the substituents $R_1$ represents a hydrogen atom, at least one of the substituents $R_2$ and $R_3$ represents an optionally substituted phenoxyl group;
- $R_1$ and $R_2$ can optionally be linked together so as to form, together with carbon atoms to which they are linked, a saturated, unsaturated or aromatic cyclic ring, or a polycyclic system containing from 4 to 6 carbon atoms, the cyclic ring or polycyclic system optionally containing one or more heteroatoms;
- $R_2$ and $R_3$ can optionally be linked together so as to form, together with carbon atoms to which they are linked, a saturated, unsaturated or aromatic cyclic ring, or a polycyclic system containing from 4 to 6 carbon atoms, the cyclic ring or polycyclic system optionally containing one or more heteroatoms;
- $R_4$ and $R_5$, which are the same or different, represent a hydrogen atom, or are selected from: i) linear or branched $C_1$-$C_8$ alkyl groups optionally containing heteroatoms, ii) optionally substituted cycloalkyl groups, iii) optionally substituted aryl groups, iv) optionally substituted linear or branched $C_1$-$C_8$ alkoxyl groups, or v) —$COOR_7$ groups or —$OCOR7$ groups in which $R_7$ is selected from linear or branched $C_1$-$C_8$ alkyl groups, or $R_7$ is a cyano group;
- $R_4$ and $R_5$ can optionally be linked together so as to form, together with carbon atoms to which they are linked, a saturated, unsaturated, or aromatic cyclic ring, or a polycyclic system containing from 4 to 6 carbon atoms, the cyclic ring or polycyclic system optionally containing one or more heteroatoms.

5. Luminescent solar concentrator according to claim 4, wherein in said general formula (I):
- Z represents a sulfur atom or an oxygen atom;
- $R_1$, which are the same, represent a hydrogen atom, or represent optionally substituted aryl groups that are selected from phenyl, 2,5-dimethylphenyl, 2,6-dimethylphenyl, 2,6-di-iso-propylphenyl, 2,5-dimethoxyphenyl, 2,6-dimethoxyphenyl, or 2,4-dimethoxyphenyl;
- $R_2$ and $R_3$, which are the same or different, represent a hydrogen atom, or are selected from: i) linear or branched $C_1$-$C_8$ alkyl groups, ii) optionally substituted aryl groups selected from phenyl, 2,6-dimethylphenyl, or 2-phenoxyphenyl, or iii) optionally substituted phenoxyl groups;
- $R_4$ and $R_5$, which are the same, represent a hydrogen atom.

6. Luminescent solar concentrator according to claim 5 wherein $R_2$ and $R_3$ are both methyl groups.

7. Photovoltaic device comprising at least one photovoltaic cell, and at least one luminescent solar concentrator including at least a disubstituted benzoheterodiazole compound of general formula (I) according to claim 5.

* * * * *